(12) United States Patent
Bernardon et al.

(10) Patent No.: US 6,924,400 B2
(45) Date of Patent: *Aug. 2, 2005

(54) TRIAROMATIC VITAMIN D ANALOGUES

(75) Inventors: Jean-Michel Bernardon, Nice (FR); Thibaud Biadatti, Opio (FR)

(73) Assignee: Galderma Research & Development, SNC, Valbonne-Sophia Antipolis (FR)

(*) Notice: Subject to any disclaimer, the term of this patent is extended or adjusted under 35 U.S.C. 154(b) by 0 days.

This patent is subject to a terminal disclaimer.

(21) Appl. No.: 10/315,121

(22) Filed: Dec. 10, 2002

(65) Prior Publication Data

US 2003/0195259 A1 Oct. 16, 2003

Related U.S. Application Data

(60) Provisional application No. 60/351,433, filed on Jan. 28, 2002.

(30) Foreign Application Priority Data

Dec. 10, 2001 (FR) .............................. 01 15924

(51) Int. Cl.[7] .............................. C07C 33/26
(52) U.S. Cl. ................ 568/811; 568/704; 568/705; 568/715; 568/807; 568/808
(58) Field of Search .............. 568/715, 807, 568/808, 825, 826

(56) References Cited

FOREIGN PATENT DOCUMENTS

| FR | 2801305 | * | 5/2001 |
| WO | WO 01/38303 A2 | | 5/2001 |

* cited by examiner

Primary Examiner—Johann Richter
Assistant Examiner—Karl Puttlitz
(74) Attorney, Agent, or Firm—Burns, Doane, Swecker & Mathis, LLP

(57) ABSTRACT

The invention relates, as novel and useful industrial products, to triaromatic compounds, which are vitamin D analogues, of general formula (I):

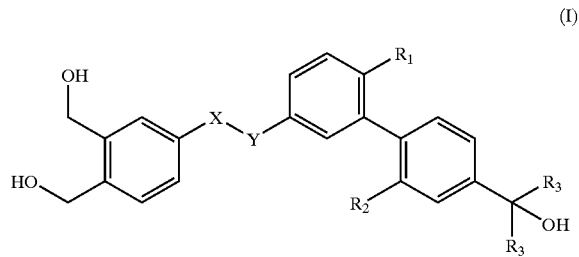

Figure 1:
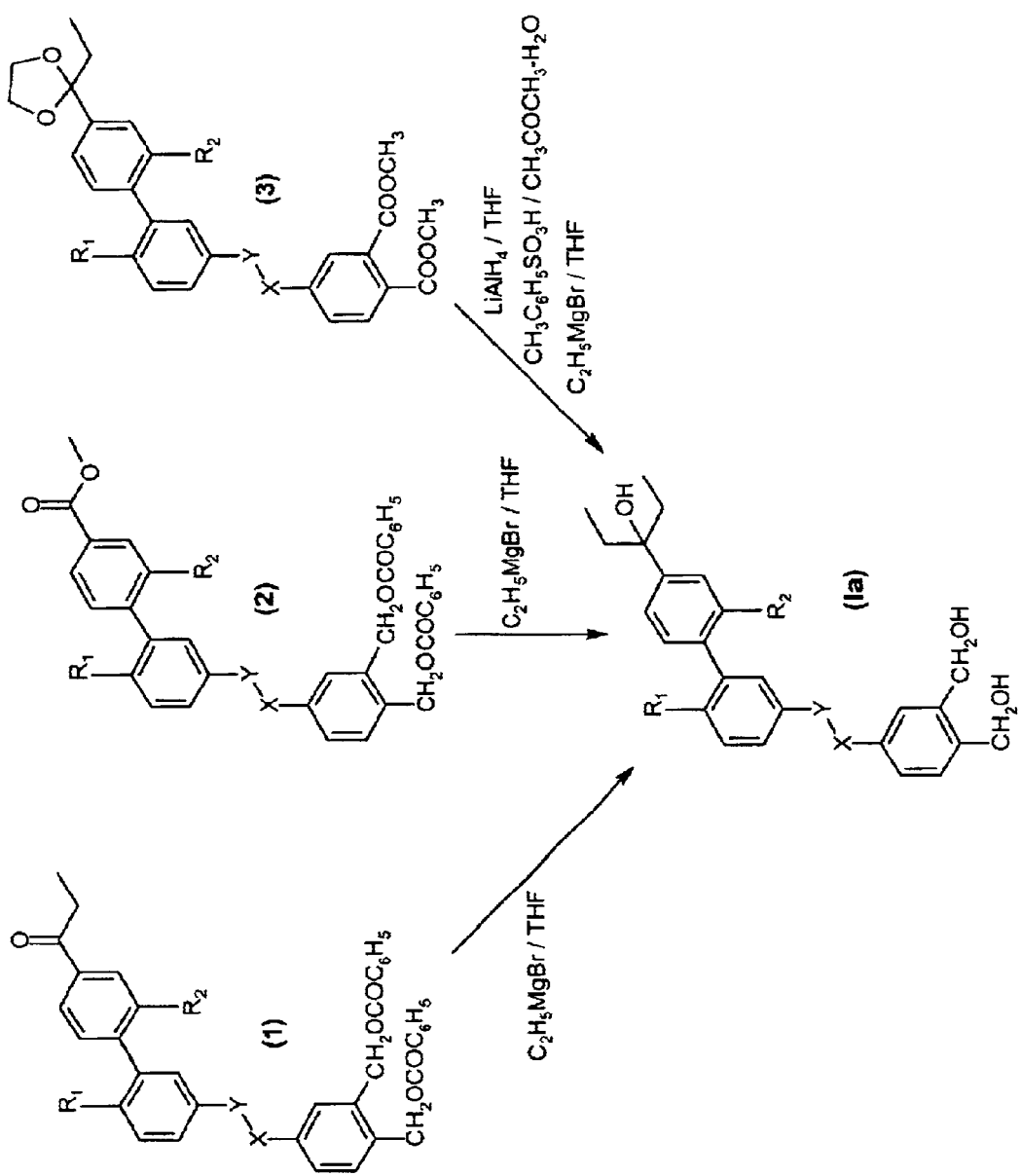

and also to a method for preparing them and to their use in pharmaceutical compositions intended for use in human or veterinary medicine, or alternatively in cosmetic compositions.

18 Claims, 7 Drawing Sheets a. DBMH, TfOH; b. Fe, AcOH; c. NaNO₂, H₂SO₄; d. NaH, EOMCl; e. BuLi, B(OiPr)₃, HCl.

a. $BH_3$; b. $MnO_2$; c. $OHCH_2CH_2OH$, TsOH; d. BuLi, $B(OiPr)_3$, HCl.

TRIAROMATIC VITAMIN D ANALOGUES

CROSS-REFERENCE TO PRIORITY/PROVISIONAL APPLICATIONS

This application claims priority under 35 U.S.C. § 119 of FR-01/15924, filed Dec. 10, 2001, and of provisional application Ser. No. 60/351,433, filed Jan. 28, 2002, both hereby expressly incorporated by reference. This application is also a continuation of said '433 provisional.

BACKGROUND OF THE INVENTION

1. Technical Field of the Invention

The invention relates, as novel and useful industrial products, to triaromatic compounds which are vitamin D analogues.

The invention also relates to a process for preparing them and to their use in pharmaceutical compositions intended for use in human or veterinary medicine, or alternatively in cosmetic compositions.

The compounds according to the invention have pronounced activity in the fields of cell proliferation and differentiation and find applications more particularly in the topical and systemic treatment of dermatological (or other) complaints associated with a keratinization disorder, complaints with an inflammatory and/or immunoallergic component and hyperproliferation of tissues of ectodermal origin (skin, epithelium, etc.), whether benign or malignant. These compounds can also be used to combat aging of the skin, whether photo-induced or chronological, and to treat cicatrization disorders.

The compounds according to the invention can also be used in cosmetic compositions for body and hair hygiene.

2. Description of the Prior Art

Vitamin D is an essential vitamin for preventing and treating mineralization defects of cartilage (rickets) and of bone (osteomalacia), and even of certain forms of osteoporosis in elderly people. However, it is now accepted that its functions extend well beyond regulating bone metabolism and calcium homeostasis. Among these functions, mention may be made of its actions on cell proliferation and differentiation and the control of the immune defenses. Their discovery has opened the way to novel therapeutic approaches in dermatology, carcinology and in the field of autoimmune diseases and that of organ or tissue transplants.

An efficient therapeutic supply has long been confounded by the toxicity of this vitamin (occasionally fatal hypercalcaemia). Structural analogues of vitamin D are currently synthesized, some of which conserve only the differentiating properties and have no action on calcium metabolism.

The Applicant has already proposed, in patent application WO 01/38303, novel compounds that are vitamin D analogues, which show selective activity on cell proliferation and differentiation without having a hypercalcaemiant nature.

SUMMARY OF THE INVENTION

The Applicant has just discovered, surprisingly, that certain compounds not specifically described in patent application WO 01/38303 show biological activity very much superior to that of the compounds specifically described. This activity is so strong that it is greater than or equal to the activity of 1,25-dihydroxyvitamin $D_3$.

Thus, the present invention relates to compounds of general formula (I) below:

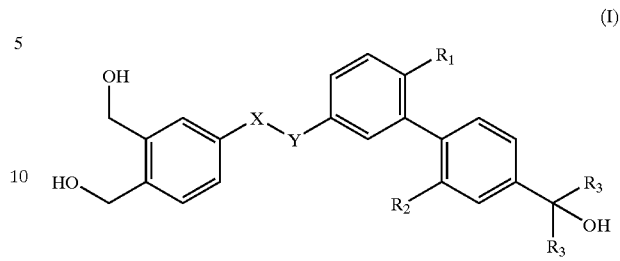

(I)

in which:
—X—Y represents a bond chosen from the following structures:
—$CH_2$—$CH_2$—
—$CH_2$—O—
—O—$CH_2$—
—$CH_2$—$N(R_4)$—
$R_4$ having the meanings given below,
$R_1$ represents a methyl radical or an ethyl radical,
$R_2$ represents an ethyl radical, a propyl radical or an isopropyl radical,
$R_3$ represents an ethyl radical or a trifluoromethyl radical,
$R_4$ represents a hydrogen atom, a methyl radical, an ethyl radical or a propyl radical,
and also to the optical and geometrical isomers thereof, and the salts thereof.

The present invention also relates to the compounds described above when they are in the form of salts of a mineral or organic acid, in particular hydrochloric acid, sulfuric acid, acetic acid, fumaric acid, hemisuccinic acid, maleic acid and mandelic acid.

DETAILED DESCRIPTION OF BEST MODE AND SPECIFIC/PREFERRED EMBODIMENTS OF THE INVENTION

Among the compounds of formula (I) falling within the context of the present invention, mention may be made especially of the following:

{5-[4'-(1-Ethyl-1-hydroxypropyl)-6-methyl-2'-propylbiphenyl-3-yloxymethyl]-2-hydroxymethylphenyl}methanol;

{5-[6,2'-Diethyl-4'-(1-ethyl-1-hydroxypropyl)biphenyl-3-yloxymethyl]-2-hydroxymethyl-phenyl}methanol;

{4-[6-Ethyl-4'-(1-ethyl-1-hydroxypropyl)-2'-propylbiphenyl-3-yloxymethyl]-2-hydroxymethylphenyl}methanol;

{4-[6-Ethyl-4'-(1-ethyl-1-hydroxypropyl)-2'-isopropylbiphenyl-3-yloxymethyl]-2-hydroxymethylphenyl}methanol;

(4-{2-[4'-(1-Ethyl-1-hydroxypropyl)-6-methyl-2'-propylbiphenyl-3-yl]ethyl}-2-hydroxymethylphenyl)methanol;

{4-[4'-(1-Ethyl-1-hydroxypropyl)-6-methyl-2'-propylbiphenyl-3-ylmethoxy]-2-hydroxymethylphenyl}methanol;

(4-{[4'-(1-Ethyl-1-hydroxypropyl)-6-methyl-2'-propylbiphenyl-3-ylamino]methyl}-2-hydroxymethylphenyl)methanol;

[4-({[4'-(1-Ethyl-1-hydroxypropyl)-6-methyl-2'-propylbiphenyl-3-yl]methylamino}methyl)-2-hydroxymethylphenyl]methanol;

[4-({Ethyl-[4'-(1-ethyl-1-hydroxypropyl)-6-methyl-2'-propylbiphenyl-3-yl]amino}methyl)-2-hydroxymethylphenyl]methanol;

[4-({[4'-(1-Ethyl-1-hydroxypropyl)-6-methyl-2'-propylbiphenyl-3-yl]propylamino}methyl)-2-hydroxymethylphenyl]methanol;
(2-Hydroxymethyl-4-{2-[6-methyl-2'-propyl-4'-(2,2,2-trifluoro-1-hydroxy-1-trifluoromethyl-ethyl)biphenyl-3-yl]ethyl}phenyl)methanol;
{2-Hydroxymethyl-4-[6-methyl-2'-propyl-4'-(2,2,2-trifluoro-1-hydroxy-1-trifluoromethyl-ethyl)biphenyl-3-yloxymethyl]phenyl}methanol;
{2-Hydroxymethyl-4-[6-methyl-2'-propyl-4'-(2,2,2-trifluoro-1-hydroxy-1-trifluoromethyl-ethyl)biphenyl-3-ylmethoxy]phenyl}methanol;
(2-Hydroxymethyl-4-{[6-methyl-2'-propyl-4'-(2,2,2-trifluoro-1-hydroxy-1-trifluoromethyl-ethyl)biphenyl-3-ylamino]methyl}phenyl)methanol;
[2-Hydroxymethyl-4-({N-methyl[6-methyl-2'-propyl-4'-(2,2,2-trifluoro-1-hydroxy-1-trifluoromethyl-ethyl)biphenyl-3-yl]amino}methyl)phenyl]methanol;
[4-({N-Ethyl[6-methyl-2'-propyl-4'-(2,2,2-trifluoro-1-hydroxy-1-trifluoromethyl-ethyl)biphenyl-3-yl]amino}methyl)-2-hydroxymethylphenyl]methanol;
[2-Hydroxymethyl-4-({[6-methyl-2'-propyl-4'-(2,2,2-trifluoro-1-hydroxy-1-trifluoromethyl-ethyl)biphenyl-3-yl]N-propyl-amino}methyl)phenyl]methanol;
(4-{2-[6-Ethyl-4'-(1-ethyl-1-hydroxypropyl)-2'-propylbiphenyl-3-yl]ethyl}-2-hydroxy-methylphenyl)methanol;
{4-[6-Ethyl-4'-(1-ethyl-1-hydroxypropyl)-2'-propylbiphenyl-3-ylmethoxy]-2-hydroxy-methylphenyl}methanol;
(4-{[6-Ethyl-4'-(1-ethyl-1-hydroxypropyl)-2'-propylbiphenyl-3-ylamino]methyl}-2-hydroxymethylphenyl)methanol;
[4-({[6-Ethyl-4'-(1-ethyl-1-hydroxypropyl)-2'-propylbiphenyl-3-yl]methylamino}methyl)-2-hydroxymethylphenyl]methanol;
[4-({Ethyl-[6-ethyl-4'-(1-ethyl-1-hydroxypropyl)-2'-propylbiphenyl-3-yl]amino}methyl)-2-hydroxymethylphenyl]methanol;
[4-({[6-Ethyl-4'-(1-ethyl-1-hydroxypropyl)-2'-propylbiphenyl-3-yl]propylamino}methyl)-2-hydroxymethylphenyl]methanol;
(4-{2-[6-Ethyl-2'-propyl-4'-(2,2,2-trifluoro-1-hydroxy-1-trifluoromethyl-ethyl)biphenyl-3-yl]ethyl}-2-hydroxymethylphenyl)methanol;
{4-[6-Ethyl-2'-propyl-4'-(2,2,2-trifluoro-1-hydroxy-1-trifluoromethyl-ethyl)biphenyl-3-yloxymethyl]-2-hydroxymethylphenyl}methanol;
{4-[6-Ethyl-2'-propyl-4'-(2,2,2-trifluoro-1-hydroxy-1-trifluoromethyl-ethyl)biphenyl-3-ylmethoxy]-2-hydroxymethylphenyl}methanol;
(4-{[6-Ethyl-2'-propyl-4'-(2,2,2-trifluoro-1-hydroxy-1-trifluoromethyl-ethyl)biphenyl-3-ylamino]methyl}-2-hydroxymethylphenyl)methanol;
[4-({[6-Ethyl-2'-propyl-4'-(2,2,2-trifluoro-1-hydroxy-1-trifluoromethyl-ethyl)biphenyl-3-yl]methylamino}methyl)-2-hydroxymethylphenyl]methanol;
[4-({N-Ethyl[6-ethyl-2'-propyl-4'-(2,2,2-trifluoro-1-hydroxy-1-trifluoromethyl-ethyl)biphenyl-3-yl]amino}methyl)-2-hydroxymethylphenyl]methanol;
[4-({[6-Ethyl-2'-propyl-4'-(2,2,2-trifluoro-1-hydroxy-1-trifluoromethyl-ethyl)biphenyl-3-yl]-N-propyl-amino}methyl)-2-hydroxymethylphenyl]methanol;
(4-{[4'-(1-Ethyl-1-hydroxypropyl)-6,2'-dimethylbiphenyl-3-ylamino]methyl}-2-hydroxymethylphenyl)methanol.

According to the present invention, the compounds of formula (I) that are more particularly preferred are those for which at least one, and preferably all, of the conditions below are satisfied:

(i) —X—Y— represents —CH$_2$—CH$_2$—;
(ii) R$_1$ is an ethyl radical;
(iii) R$_2$ is a propyl radical;
(iv) R$_3$ is an ethyl radical.

A Subject of the present invention is also processes for preparing the compounds of formula (I) according to the reaction schemes presented in FIG. 1.

Figure 2:
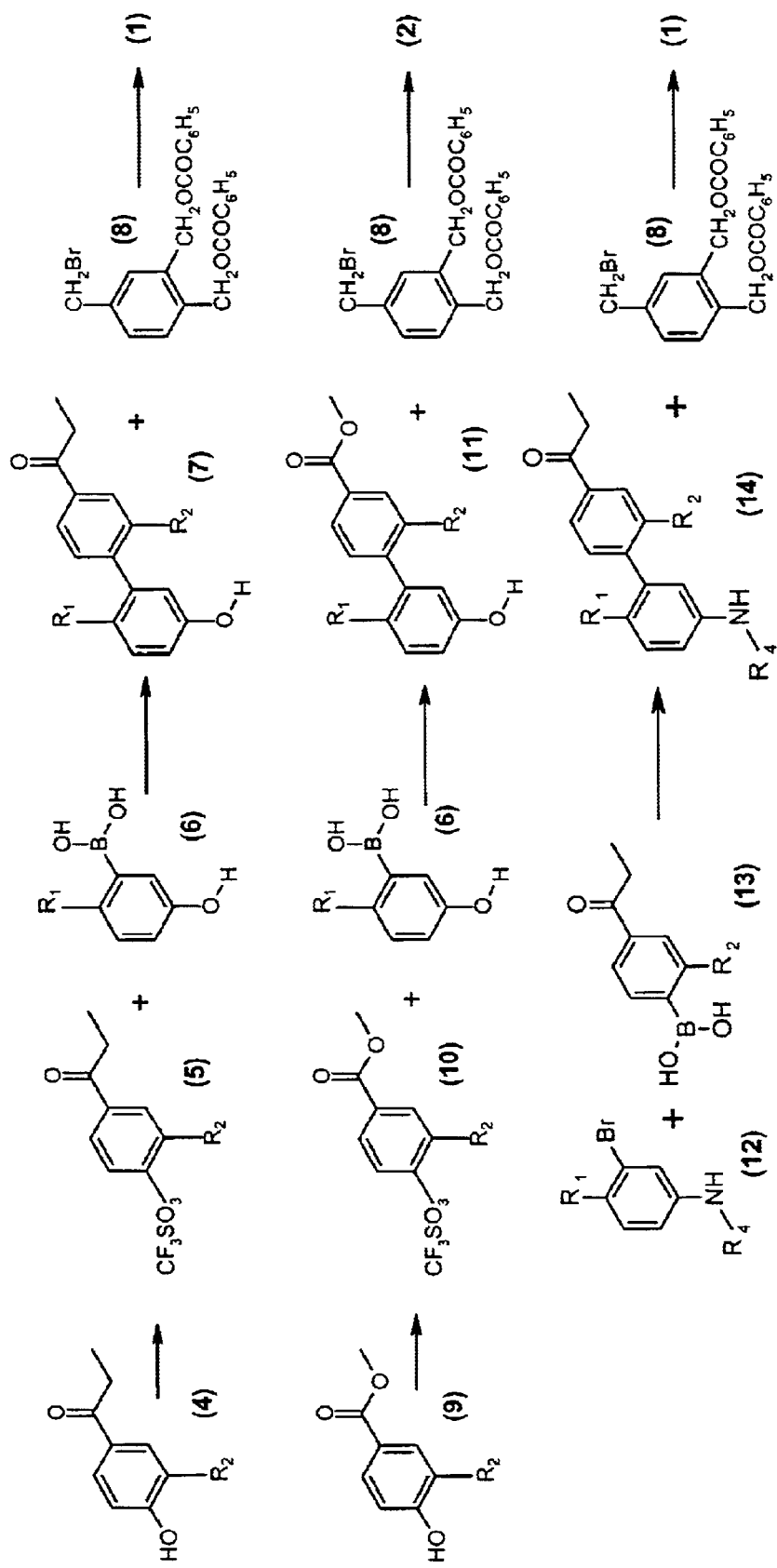

When —X—Y— represents a bond of structure —CH$_2$—O— or —CH$_2$—N(R$_4$)—, the compounds of formula (Ia) are preferably prepared from compounds (1) and (2), obtained according to the reaction schemes of FIG. 2.

The compounds (1) (when Y=O) and (2) may be obtained, respectively, from compounds (4) and (9), firstly by forming the trifluoromethanesulfonate derivatives ((5) and (10), respectively) in the presence of trifluoromethanesulfonic anhydride and a base such as triethylamine in dichloromethane. Next, by means of a Suzuki coupling reaction with the boronic acid derivatives (6) in the presence of a catalyst such as tetrakis(triphenylphosphine)palladium (0), the derivatives (7) and (11) are respectively obtained, followed by a coupling reaction with the bromo derivatives (8) in the presence of potassium carbonate in methyl ethyl ketone. When Y=NR$_4$, compound (1) may be obtained from compound (12), firstly by a Suzuki coupling reaction with the boronic acid derivative (13) in the presence of a catalyst such as tetrakis(triphenylphosphine)palladium (0), to give the derivative (14), followed by a coupling reaction with the bromo derivatives (8) in the presence of sodium hydride in dimethylformamide.

Figure 3:
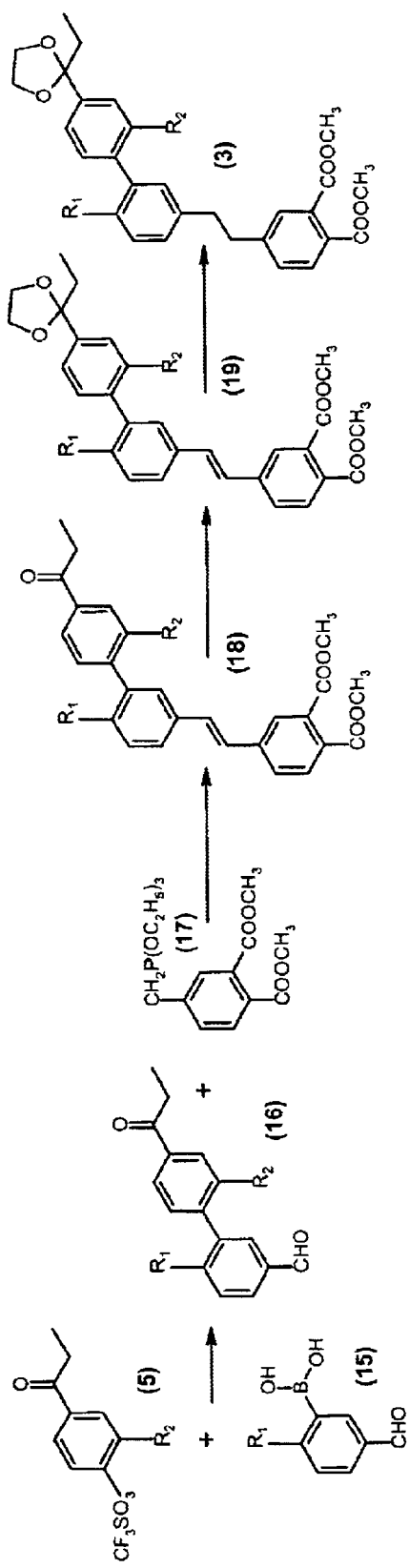

When —X—Y— represents a bond of structure —CH$_2$—CH$_2$—, the compounds of formula (Ia) shown in FIG. 1 are prepared from the compounds (3), obtained according to the reaction scheme shown in FIG. 3.

Via a Suzuki reaction of the trifluoromethanesulfonate derivatives (5) with the boronic acid derivatives (15) in the presence of a catalyst such as tetrakis(triphenylphosphine) palladium(0) and a base such as potassium carbonate in a solvent such as 1,2-dimethoxyethane, the compounds (16) are obtained. These compounds are converted into the compounds (18) by a Horner-Emmons reaction with compound (17), and then into the compounds (19) by protecting the ketone function in dioxolane form (ethylne glycol, para-toluenesulfonic acid, toluene). Reduction of the double bond in the presence of palladium-on-charcoal in a solvent such as methanol gives the compounds (3).

Figure 4:
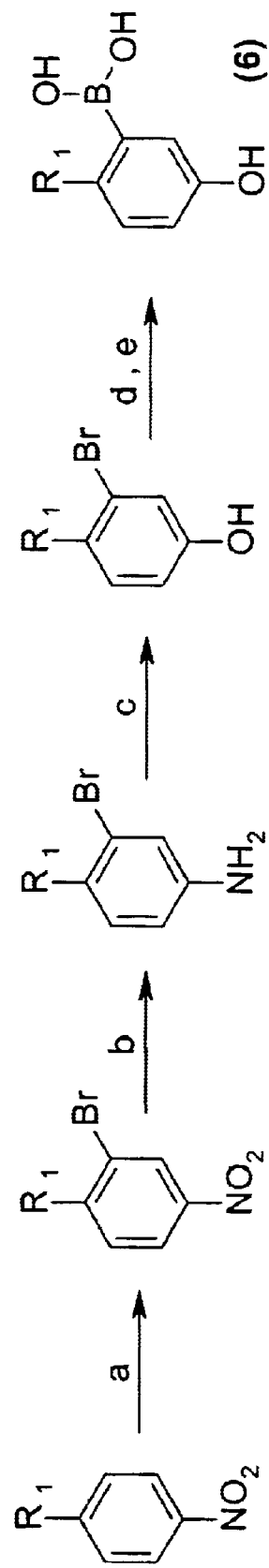
Figure 5:
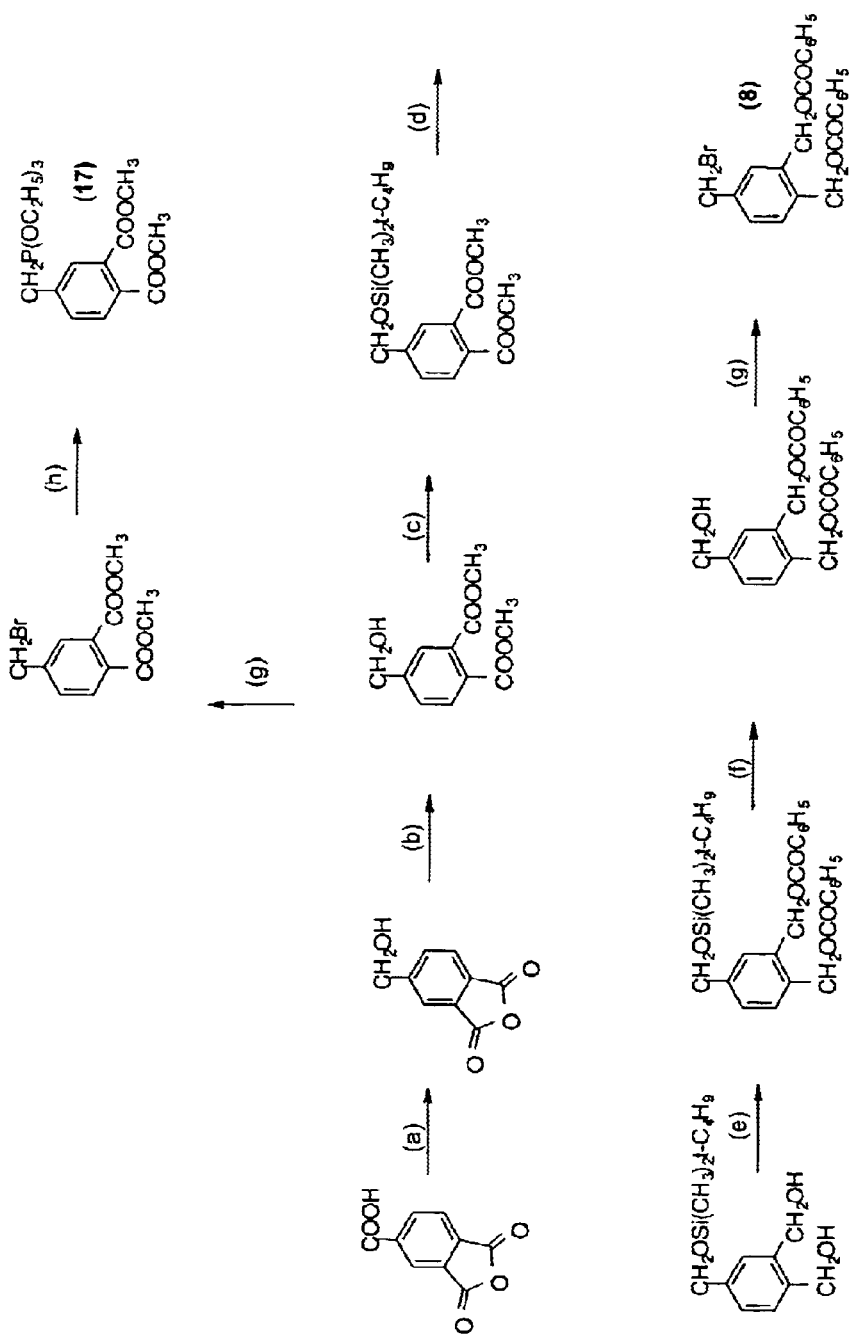
Figure 6:
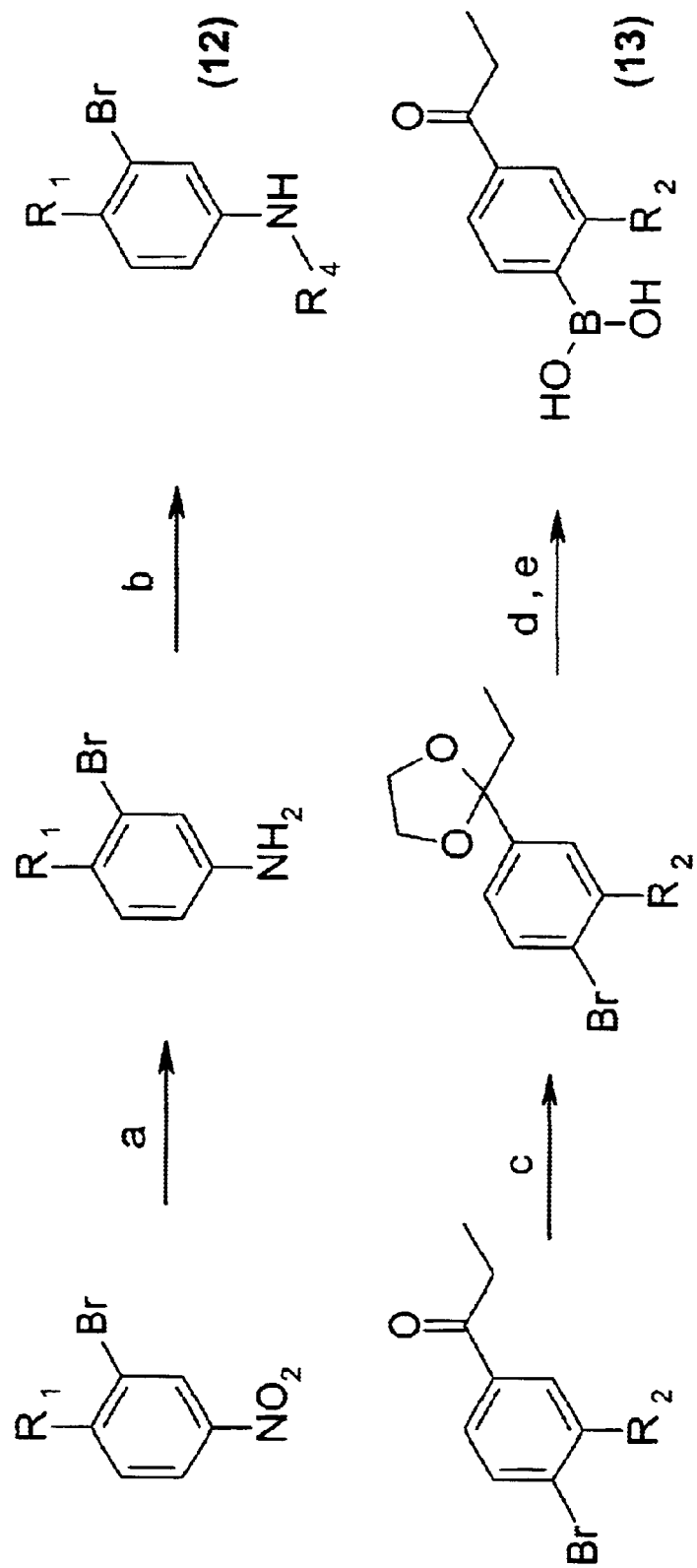
Figure 7:
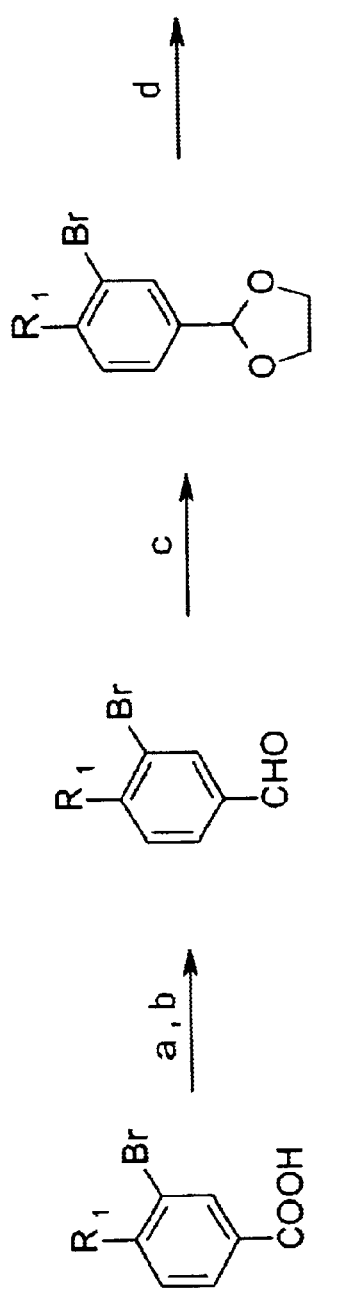

Compound (6) may be obtained according to the reaction scheme of FIG. 4. Compounds (8) and (17) may be obtained according to the reaction scheme of FIG. 5. Compounds (12) and (13) may be obtained according to the reaction scheme of FIG. 6. Compound (15) may be obtained according to the reaction scheme of FIG. 7.

When R$_3$ represents a trifluoromethyl radical, the compounds (I) may be obtained from the corresponding bromo derivative by formation of the organomagnesium or organolithium derivative followed by reaction with hexafluoroacetone.

The compounds according to the invention show biological properties analogous to those of vitamin D, especially properties of transactivation of the vitamin D response elements (VDRE), such as agonist or antagonist activity with respect to receptors of vitamin D or its derivatives. The expression "D vitamins or derivatives thereof" means, for example, the derivatives of vitamin D$_2$ or D$_3$ and in particular 1,25-dihydroxyvitamin D$_3$ (calcitriol).

This agonist activity with respect to receptors of vitamin D or of derivatives thereof may be demonstrated "in vitro"

by methods known in the field of study of gene transcription (Hansen et al., The Society For Investigative Dermatology, vol.1, No. 1, April 1996).

The biological properties analogous to vitamin D may also be measured by means of the capacity of the product to induce the differentiation of promyelocytic leukemia cells HL60. The protocol and also the results obtained with the compounds according to the invention are described in Example 8 of the present patent application.

By way of example, the VDR agonist activity may be tested on the HeLa cell line by cotransfection of an expression vector of the human VDR receptor and of the reporter plasmid p240Hase-CAT. The agonist activity may also be characterized in this cotransfection system, by determining the dose required to achieve 50% of the maximum activity of the product (AC50). The details of the protocol for this test and the results obtained with the compounds according to the invention are described in Example 9 of the present patent application.

The biological properties analogous to vitamin D may also be measured by means of the capacity of the product to inhibit the proliferation of normal human keratinocytes (NHK in culture). The product is added to NHKs cultured under conditions promoting the proliferative state. The product is left in contact with the cells for five days. The number of proliferative cells is measured by incorporation of bromodeoxyuridine (BRdU) into the DNA. The protocol for this test and the results obtained with the compounds according to the invention are described in Example 10 of the present patent application.

A subject of the present invention is also, as a medicinal product, the compounds described above. The compounds according to the invention are particularly suitable in the following fields of treatment:

1) for treating dermatological complaints associated with a differentiation or proliferation disorder of keratinocytes or sebocytes, especially for treating common acne, comedones, polymorphonuclear leukocytes, acne rosacea, nodulocystic acne, acne conglobata, senile acne and secondary acnes such as solar acne, acne medicamentosa or occupational acne;
2) for treating keratinization disorders, especially ichthyosis, ichthyosiform conditions, Darier's disease, palmoplantar keratoderma, leukoplakia and leukoplakiform conditions, and cutaneous or mucous (buccal) lichen;
3) for treating other dermatological complaints associated with a keratinization disorder with an inflammatory and/or immunoallergic component, and especially all forms of psoriasis, whether cutaneous, mucous or ungual psoriasis, and even psoriatic rheumatism, or alternatively cutaneous atopy, such as eczema or respiratory atopy, or alternatively gingival hypertrophy;
4) for treating certain inflammatory complaints not showing a keratinization disorder, such as atopic eczema and contact allergies;
5) for treating all dermal or epidermal proliferations, whether benign or malignant, and whether of viral origin or not, such as common warts, flat warts and verruciform epidermodysplasia, oral or florid papillomatoses and proliferations that may be induced by ultraviolet radiation, especially in the case of basocellular and spinocellular epithelioma;
6) for treating other dermatological disorders such as bullous dermatosis and collagen diseases;
7) for preventing or treating the signs of aging of the skin, whether photo-induced or chronological aging, or for reducing actinic keratosis and pigmentations, or any cutaneous pathologies associated with chronological or actinic aging;
8) for preventing or treating cicatrization disorders or for preventing or repairing stretch marks;
9) for controlling sebaceous function disorders such as acneic hyperseborrhoea or simple seborrhoea or alternatively seborrhoeic eczema;
10) for treating certain ophthalmological disorders, especially corneopathies;
11) in the treatment or prevention of cancerous or precancerous conditions of cancers presenting or being able to be induced to present vitamin D receptors, such as, but without limitation, breast cancer, leukaemia, myelodysplasic syndromes and lymphomas, carcinomas of the cells of the malpighian epithelium and gastrointestinal cancers, melanomas and osteosarcoma;
12) in the treatment of inflammatory complaints such as arthritis or rheumatoid arthritis;
13) in the treatment of any cutaneous or general complaint of viral origin;
14) in the prevention or treatment of alopecia of various origins, especially chemotherapy-induced or radiation-induced alopecia;
15) in the treatment of dermatological or general complaints with an immunological component;
16) in the treatment of immune complaints, such as autoimmune diseases (for instance, but without limitation, type 1 sugar diabetes, multiple sclerosis, lupus and lupus-type complaints, asthma, glomerulonephritis, etc.), selective dysfunctions of the immune system (for example AIDS) and the prevention of immune rejection [for instance graft rejections (for example kidney, heart, bone marrow, liver, pancreatic islets or the whole pancreas, the skin, etc.) or the prevention of graft-versus-host disease];
17) in the treatment of endocrine complaints, given that the vitamin D analogues can modulate hormonal secretion, such as increasing the secretion of insulin or selectively suppressing the secretion of parathyroid hormone (for example in chronic renal insufficiency and secondary hyperparathyroidism);
18) in the treatment of complaints characterized by abnormal management of intracellular calcium; and
19) in the treatment and/or prevention of vitamin D deficiencies and other complaints of homeostasis of minerals in the plasma and the bones, such as rickets, osteomalacia, osteoporosis, especially in the case of menopausal women, renal osteodystrophy and parathyroid function disorders.

A subject of the present invention is also a pharmaceutical composition comprising at least one compound as defined above in a pharmaceutically acceptable support.

The compounds according to the invention may be administered enterally, parenterally, topically or ocularly.

Via the enteral route, the pharmaceutical compositions may be in the form of tablets, gel capsules, sugar-coated tablets, syrups, suspensions, solutions, powders, granules, emulsions, or suspensions of polymeric or lipid vesicles or nanospheres or microspheres allowing controlled release.

Via the parenteral route, the compositions may be in the form of solutions or suspensions for infusion or for injection.

The compounds according to the invention are generally administered at a daily dose of about from 0.001 $\mu$g/kg to 1000 $\mu$g/kg and preferably of about from 0.01 $\mu$g/kg to 100 $\mu$g/kg of body weight in 1 to 3 dosage intakes.

Via the topical route, the pharmaceutical compositions based on compounds according to the invention are intended for treating the skin, the scalp and mucous membranes and are in the form of ointments, creams, milks, pomades, powders, impregnated pads, solutions, gels, sprays, lotions or suspensions. They may also be in the form of suspensions of polymeric or lipid vesicles or nanospheres or microspheres or polymeric patches and hydrogels allowing controlled release. These topical-route compositions may be either in anhydrous form or in aqueous form depending on the clinical indication.

Via the ocular route, they are mainly eye lotions.

These compositions for the topical or ocular route contain at least one compound according to the invention in a concentration preferably of between 0.0001% and 5% and preferably between 0.001% and 1% relative to the total weight of the composition.

The compounds according to the invention also find an application in cosmetics, in particular in body and hair hygiene and especially for treating acne-prone skin, for regrowth of the hair, or for preventing hair loss, for controlling the greasy appearance of the skin or the hair, in protecting against the harmful effects of sunlight or in the treatment of dry skin, and for preventing and/or treating photo-induced or chronological aging of the skin.

The present invention is thus also directed towards a cosmetic composition containing, in a cosmetically acceptable support, at least one compound as defined above.

This cosmetic composition may especially be in the form of a cream, a milk, a lotion, a gel, a suspension of polymeric or lipid vesicles or nanospheres or microspheres, a soap or a shampoo.

The concentration of compound of general formula (I) in the cosmetic composition according to the invention may be between 0.001% and 3% by weight relative to the total weight of the composition.

In the pharmaceutical and cosmetics fields, the compounds according to the invention may advantageously be used in combination with inert additives or even pharmacodynamically or cosmetically active additives or combinations of these additives, and especially:
wetting agents;
flavor enhancers;
preserving agents such as para-hydroxybenzoic acid esters;
stabilizers;
moisture regulators;
pH regulators;
osmotic pressure modifiers;
emulsifiers;
UV-A and UV-B screening agents;
antioxidants such as α-tocopherol, butylhydroxyanisole, butylhydroxytoluene, superoxide dismutase, ubiquinol or certain metal-chelating agents;
depigmenting agents such as hydroquinone, azelaic acid, caffeic acid or kojic acid;
emollients;
moisturizers, for instance glycerol, PEG 400, thiamorpholinone and its derivatives or urea;
antiseborrhoeic or antiacne agents, such as S-carboxymethylcysteine, S-benzyl-cysteamine, salts thereof and derivatives thereof, or benzoyl peroxide;
antibiotics, for instance erythromycin and its esters, neomycin, clindamycin and its esters, and tetracyclines;
antifungal agents such as ketoconazole or poly-4,5-methylne-3-isothiazolinones;
agents for promoting regrowth of the hair, for instance Minoxidil (2,4-diamino-6-piperidinopyrimidine 3-oxide) and its derivatives, Diazoxide (7-chloro 3-methyl-1,2,4-benzothiadiazine 1,1-dioxide) and Phenytoin (5,4-diphenylimidazolidine-2,4-dione);
non-steroidal anti-inflammatory agents;
carotenoids and especially β-carotene;
anti-psoriatic agents such as anthralin and its derivatives;
eicosa-5,8,11,14-tetraynoic acid and eicosa-5,8,11-triynoic acid, and esters and amides thereof;
retinoids, i.e., natural or synthetic RAR or RXR receptor ligands;
corticosteroids or oestrogens;
α-hydroxy acids and α-keto acids or derivatives thereof, such as lactic acid, malic acid, citric acid, glycolic acid, mandelic acid, tartaric acid, glyceric acid or ascorbic acid, and also salts, amides or esters thereof, or β-hydroxy acids or derivatives thereof, such as salicylic acid and its salts, amides or esters;
ion-channel blockers such as potassium-channel blockers;
or alternatively, more particularly for pharmaceutical compositions, in combination with medicinal products known to interfere with the immune system (for example cyclosporin, FK 506, glucocorticoids, monoclonal antibodies, cytokines or growth factors, etc.).

Needless to say, a person skilled in the art will take care to select the optional compound(s) to be added to these compositions such that the advantageous properties of the compounds of the present invention are not, or are not substantially, adversely affected by the envisaged addition.

Examples of the production of the active compounds of general formula (I) according to the invention, and also various concrete formulations based on such compounds and tests to evaluate the biological activity of the compounds according to the invention, will now be given, for illustrative purposes and with no limiting nature.

EXAMPLE 1
{5-[4'-(1-Ethyl-1-hydroxypropyl)-6-methyl-2'-propylbiphenyl-3-yloxy-methyl]-2-hydroxymethylphenyl}methanol.
(a) 1-(4-Hydroxy-3-propylphenyl)propan-1-one 7.1 g (53 mmol) of aluminum chloride are placed in 70 ml of nitrobenzene in a round-bottomed flask and under a stream of nitrogen. The mixture is heated at 70° C. until dilution is complete. It is then cooled to 0° C. and 7.2 ml (52 mmol) of 2-propylphenol are added. The mixture is allowed to warm to room temperature and is then heated to 40° C. 4.6 ml (52 mmol) of propionyl chloride are then added dropwise. The reaction medium is heated at 40° C. for 2 hours and then stirred for 48 hours at room temperature. It is then poured onto ice with 20 ml of concentrated hydrochloric acid. After extraction with ethyl ether, the organic phase is washed with 2N sodium hydroxide. The aqueous phases are acidified with hydrochloric acid and extracted with ether. The organic phase is dried over magnesium sulfate, filtered and then evaporated. The black solid obtained is triturated in heptane, filtered off and dried. 3.5 g (35%) of the expected product are obtained in the form of a black powder.
(b) 4-Propionyl-2-propylphenyl 1,1,1-trifluoromethanesulfonate 3.4 g (18 mmol) of 1-(4-hydroxy-3-propylphenyl)-1-propanone are placed in 100 ml of dichloromethane in a round-bottomed flask and under a stream of nitrogen. The reaction medium is cooled to 0° C. and 3.3 ml (23 mmol) of triethylamine are then added. 15 minutes later, 4.3 ml (26 mmol) of trifluoromethanesulfonic anhydride are added. 1 hour later, the mixture is poured into saturated aqueous ammonium chloride solution and extracted with dichloromethane. The organic phase is dried over magnesium sulfate, filtered and then evaporated. The residue obtained is purified by chromatography on a column of silica eluted with a mixture of heptane and ethyl acetate (70/30). After evaporating off the solvents, 5.4 g (93%) of the expected product are obtained in the form of a brown oil.

(c) 3-Bromo-4-methylphenylamine 30 g (139 mmol) of 2-bromo-4-nitrotoluene are placed in 180 ml of water, 400 ml of ethanol and 110 ml of acetic acid in a round-bottomed flask and under a stream of nitrogen. The medium is heated to 70° C. and 31 g (556 mmol) of iron are added portionwise. The mixture is refluxed for 2 hours and, after cooling, 180 ml of 34% aqueous ammonia are added slowly. The mixture is filtered through Celite and the organic phase is extracted with water and ethyl acetate. It is then dried over magnesium sulfate, filtered and then evaporated. 25.5 g (100%) of the expected product are obtained in the form of a brown oil.

(d) 3-Bromo-4-methylphenol 25 g (134 mmol) of 2-bromo-4-aminotoluene are placed in 400 ml of 1M sulfuric acid in a round-bottomed flask, and the mixture is then cooled to 0° C. 13 g (190 mmol) of sodium nitrite dissolved in 30 ml of water are added, followed by addition of 21 ml of concentrated sulfuric acid. The mixture is refluxed for 4 hours. It is then extracted with ethyl ether. The organic phase is dried over magnesium sulfate, filtered and then evaporated. The residue obtained is purified by chromatography on a column of silica eluted with a mixture of heptane and ethyl acetate (90/10) to give 12.1 g (48%) of the expected product in the form of a brown oil.

(e) 2-Bromo-4-ethoxymethoxy-1-methylbenzene 12.1 g (65 mmol) of 3-bromo-4-methylphenol are placed in 100 ml of dry dimethylformamide in a round-bottomed flask and under a stream of nitrogen. At 0° C., 3.1 g (78 mmol) of 60% sodium hydride are added slowly. After 1 hour, 7.3 ml (78 mmol) of methoxyethyl chloride are added dropwise. The mixture is stirred at room temperature overnight. It is then poured into water and extracted with ethyl acetate. The organic phase is dried over magnesium sulfate, filtered and then evaporated. The residue obtained is purified by chromatography on a column of silica eluted with a mixture of heptane and ethyl acetate (85/15) to give 13.2 g (83%) of the expected product in the form of an oil.

(f) 5-Ethoxymethoxy-2-methylphenylboronic acid 1.4 g (59 mmol) of magnesium turnings are placed in tetrahydrofuran in a round-bottomed flask and under a stream of nitrogen. 13.2 g (54 mmol) of 2-bromo-4-ethoxymethoxy-1-methylbenzene diluted in a small amount of THF are added slowly. The medium is refluxed for 20 minutes. It is then added via a cannula to 15 ml (65 mmol) of triisopropyl borate. The mixture sets to a solid and is then poured into 1N hydrochloric acid solution and extracted with ether. The organic phase is dried over magnesium sulfate, filtered and then evaporated. 9.8 g (87%) of the expected product are obtained in the form of a brown oil.

(g) 1-(5'-Ethoxymethoxy-2'methyl-2-propylbiphenyl-4-yl)propan-1-one 1.56 g (7.4 mmol) of 5-ethoxymethoxy-2-methylphenylboronic acid, 2 g (6.2 mmol) of 4-propionyl-2-propylphenyl 1,1,1-trifluoromethanesulfonate, 517 mg (12 mmol) of lithium chloride and 7.4 ml of 2M potassium carbonate solution are dissolved in 50 ml of 1,2-dimethoxyethane in a round-bottomed flask and under a stream of nitrogen. The mixture is refluxed for 10 hours. It is then poured into water and extracted with ethyl acetate. The organic phase is dried over magnesium sulfate, filtered and then evaporated. A brown oil is obtained, which is used without further purification for the rest of the synthesis.

(h) 1-(5'-Hydroxy-2'-methyl-2-propylbiphenyl-4-yl)propan-1-one. CS 755.064

1-(5'-Ethoxymethoxy-2'-methyl-2-propylbiphenyl-4-yl)propan-1-one, obtained in step (g), is dissolved in methanol and a few drops of sulfuric acid are added. Stirring is continued overnight and the medium is then extracted with ethyl acetate and water. The organic phase is dried over magnesium sulfate, filtered and then evaporated. The residue obtained is purified by chromatography on a column of silica eluted with a mixture of heptane and ethyl acetate (75/25) to give 1.53 g (88%) of the expected product in the form of a brown oil.

(i) Dimethyl 4-hydroxymethylphthalate 50 g (260 mmol) of trimellitic anhydride are placed in 500 ml of dioxane in a round-bottomed flask and under a stream of nitrogen. 520 ml (520 mmol) of borane (1M/THF) are added dropwise and the mixture is stirred for 48 hours at room temperature. The reaction medium is then poured slowly into saturated aqueous ammonium chloride solution and extracted with dichloromethane. The organic phase is dried over magnesium sulfate, filtered and then evaporated. The residue is dissolved in 400 ml of methanol and 5 ml of sulfuric acid are added. The resulting mixture is heated at 80° C. overnight. The methanol is evaporated off and the residue is taken up in ethyl acetate and washed with water. The organic phase is dried over magnesium sulfate, filtered and then evaporated. 52.7 g (90%) of the expected product are obtained in the form of a yellow oil.

(j) Dimethyl 4-(tert-butyldimethylsilanyloxymethyl)phthalate 19 g (84.8 mmol) of dimethyl 4-hydroxymethylphthalate are placed in 250 ml of dimethylformamide in a round-bottomed flask and under a stream of nitrogen. 14 g (93 mmol) of tert-butyldimethylsilyl chloride and 8 g (118 mmol) of imidazole are added. The reaction medium is stirred for 3 hours at room temperature, it is then concentrated and the residue is dissolved in ether and then filtered. The filtrate is evaporated and the product is purified by chromatography on a column of silica eluted with a mixture of heptane and ethyl acetate (50/50) to give 23.7 g (83%) of the expected product in the form of a yellow oil.

(k) [4-(tert-Butyldimethylsilanyloxymethyl)-2-hydroxymethylphenyl]methanol 17.8 g (469 mmol) of lithium aluminum hydride are placed in 800 ml of ethyl ether in a round-bottomed flask and under a stream of nitrogen. At 0° C., a solution of 66.4 g (196 mmol) of dimethyl 4-(tert-butyldimethylsilanyloxymethyl)phthalate in 200 ml of ether and 100 ml of THF is added dropwise. The reaction medium is stirred at 0° C. for 2 hours. 18 ml of water, 18 ml of 15% sodium hydroxide solution and then 54 ml of water are added very slowly. The precipitate formed is filtered off and rinsed with ether, and the filtrate is evaporated. 52 g (94%) of the expected product are obtained in the form of a colorless oil.

(l) 2-Benzoyloxymethyl-4-(tert-butyldimethylsianyloxymethyl)benzyl benzoate 40 g (141 mmol) of [4-(tert-butyldimethylsilanyloxymethyl)-2-hydroxymethylphenyl]methanol are placed in 400 ml of THF in a round-bottomed flask and under a stream of nitrogen. At 0° C., 49 ml (352 mmol) of triethylamine are added, followed by dropwise addition of 34.5 ml (297 mmol) of benzoyl chloride. The reaction medium precipitates and 350 mg (2.8 mmol) of dimethylaminopyridine are then added. The mixture is allowed to warm to room temperature overnight. The medium is filtered and the solid is washed with ethyl acetate. The filtrate is evaporated and the residue is taken up in dichloromethane. The organic phase is washed with saturated aqueous ammonium chloride solution and then with water. It is then dried over magnesium sulfate, filtered and evaporated. 69.5 g (100%) of the expected product are obtained in the form of an orange-colored oil.

(m) 2-Benzoyloxymethyl-4-hydroxymethylbenzyl benzoate 69 g (140 mmol) of 2-benzoyloxymethyl-4-(tert-butyldimethylsilanyloxymethyl)benzyl benzoate are placed in 450 ml of ethyl acetate in a round-bottomed flask and under a stream of nitrogen. 178 ml of tetrabutylammonium fluoride (1M/THF) are added. The medium is stirred for 30 minutes at room temperature. It is then poured into saturated aqueous ammonium chloride solution and extracted with ethyl acetate. The organic phase is dried over magnesium sulfate, filtered and then evaporated. The residue is purified by chromatography on a column of silica eluted with a mixture of heptane and ethyl acetate (40/60) to give 46.6 g (88%) of the expected product in the form of a white powder with a melting point of 92° C.

(n) 3,4-bis(benzoyloxymethyl)benzyl bromide 40 g (106 mmol) of 2-benzoyloxymethyl-4-hydroxymethylbenzyl benzoate are placed in 500 ml of dichloromethane and 77.6 g (234 mmol) of carbon tetrabromide in a round-bottomed flask and under a stream of nitrogen. At 0° C., a solution of 61.3 g (233 mmol) of triphenylphosphine in 200 ml of dichloromethane is added dropwise. The mixture is allowed to warm to room temperature over 2 hours. The reaction medium is poured into water and extracted with dichloromethane. The organic phase is dried over magnesium sulfate, filtered and then evaporated. The residue is purified by chromatography on a column of silica eluted with a mixture of heptane and ethyl acetate (70/30) to give 32.6 g (70%) of the expected product in the form of a white powder.

(o) 1-{5'-[3,4-Bis(benzoyloxymethyl)benzyloxy]-2'methyl-2-propylbiphenyl-4-yl}-1-propanone 1.5 g (5.4 mmol) of 1-(5'-hydroxy-2'-methyl-2-propylbiphenyl-4-yl)-1-propanone, 2.5 g (5.7 mmol) of (3,4-bis(benzoyloxymethyl)benzyl bromide and 750 mg (5.4 mmol) of potassium carbonate are placed in 50 ml of methyl ethyl ketone in a round-bottomed flask and under a stream of nitrogen. The mixture is refluxed overnight and, after cooling, it is filtered through Celite. The filtrate is extracted with water and ethyl acetate. The organic phase is dried over magnesium sulfate, filtered and then evaporated. The residue obtained is purified by chromatography on a column of silica eluted with a mixture of heptane and ethyl acetate (85/15) to give 1.93 g (56%) of the expected product in the form of a dark yellow oil.

(p) 1-{5'-[3,4-Bis(hydroxymethyl)benzyoxyl]-2'methyl-2-propylbiphenyl-4-yl}-1-propanone 1.9 g (3 mmol) of 1-{5'-[3,4-bis(benzoyloxymethyl) benzyloxy]-2'-methyl-2-propylbiphenyl-4-yl}-1-propanone are dissolved in 40 ml of methanolic 2% potassium carbonate solution in a round-bottomed flask. The mixture is stirred at room temperature overnight. It is then poured into water and extracted with ethyl acetate. The organic phase is dried over magnesium sulfate, filtered and then evaporated. The residue obtained is purified by chromatography on a column of silica eluted with a mixture of heptane and ethyl acetate (70/30) to give 890 mg (69%) of the expected product.

(q) {5-[4'(1-Ethyl-1-hydroxypropyl)-6-methyl-2'-propylbiphenyl-3-yloxymethyl]-2-hydroxymethylphenyl}methanol 890 mg (2 mmol) of 1-{5'-[3,4-bis(hydroxymethyl) benzyloxy]-2'-methyl-2-propylbiphenyl-4-yl}-1-propanone are placed in 40 ml of dry THF in a round-bottomed flask and under a stream of nitrogen. At 0° C., 4.1 ml (12 mmol) of ethylmagnesium bromide are added. The reaction medium is stirred at room temperature for 1 hour 30 minutes and then poured into saturated aqueous ammonium chloride solution and extracted with ethyl acetate. The organic phase is dried over magnesium sulfate, filtered and then evaporated. The residue obtained is purified by chromatography on a column of silica eluted with a mixture of heptane and ethyl acetate (50/50) to give 550 mg (64%) of {5-[4'-(1-ethyl-1-hydroxypropyl)-6-methyl-2'-propylbiphenyl-3-yloxymethyl]-2-hydroxymethylphenyl}methanol in the form of white crystals with a melting point of 97° C.

EXAMPLE 2

{5-[6,2'-Diethyl-4'-(1-ethyl-1-hydroxypropyl)biphenyl-3-yloxymethyl]-2-hydroxymethylphenyl}methanol (a) 4-Bromo-2-ethylphenol 5.57 g (45 mmol) of 2-ethylphenol are placed in 250 ml of chloroform in a round-bottomed flask and under a stream of nitrogen. 43.4 g (90 mmol) of tetrabutylammonium tribromide are added portionwise. The medium is stirred for 1 hour at room temperature and is then hydrolysed with saturated aqueous sodium thiosulfate solution. The organic phase is washed with water, dried over magnesium sulfate, filtered and then evaporated. 9.1 g (100%) of the expected product are obtained in the form of a yellow oil.

(b) (4-Bromo-2-ethylphenoxy)-tert-butyldimethylsilane

In a manner similar to that of Example 1(j), starting with 9.1 g (45 mmol) of 4-bromo-2-ethylphenol, and after purification by chromatography on a column of silica eluted with heptane, 11.9 g (83%) of the expected product are obtained in the form of a colorless oil.

(c) 1-[4-(tert-Butyldimethylsilanyloxy)-3-ethylphenyl]propan-1-ol 11.9 g (38 mmol) of (4-bromo-2-ethylphenoxy)-tert-butyldimethylsilane are placed in 200 ml of THF in a round-bottomed flask and under a stream of nitrogen. The reaction medium is cooled to −78° C. and 16.6 ml (41 mmol) of n-butyllithium (2.5 M/THF) are added dropwise. 30 minutes later, 3.2 ml (45 mmol) of propionaldehyde are added dropwise. The medium is stirred for 3 hours at −78° C. It is then poured into saturated aqueous ammonium chloride solution and extracted with ethyl acetate. The organic phase is dried over magnesium sulfate, filtered and then evaporated. 11.1 g (100%) of the expected product are obtained in the form of a colorless oil.

(d) 1-[4-(tert-Butyldimethylsilanyloxy)-3-ethylphenyl]propan-1-one 11.1 g (37 mmol) of 1-[4-(tert-butyldimethylsilanyloxy)-3-ethylphenyl]propan-1-ol are placed in 100 ml of dichloromethane in a round-bottomed flask, and 32.8 g (377 mmol) of manganese dioxide are added. The medium is stirred overnight at room temperature. It is then filtered through Celite and rinsed with dichloromethane. The filtrate is evaporated and the residue is purified by chromatography on a column of silica eluted with a mixture of heptane and ethyl acetate (90/10) to give 6.8 g (62%) of the expected product in the form of an orange-colored oil.

(e) 1-(3-Ethyl-4-hydroxyphenyl)propan-1-one

In a manner similar to that of Example 1(m), starting with 6.8 g (23 mmol) of 1-[4-(tert-butyldimethylsilanyloxy)-3-ethylphenyl]propan-1-one in 50 ml of THF, 4.1 g (100%) of the expected product are obtained in the form of a beige-colored oil.

(f) 2-Ethyl-4-propionylphenyl 1,1,1-trifluoromethanesulfonate

In a manner similar to that of Example 1(b), by reacting 4.6 g (26.3 mmol) of 1-(3-ethyl-4-hydroxyphenyl)propan-1-one with 4.8 ml (28.9 mmol) of trifluoromethanesulfonic anhydride, 8.1 g (99%) of the expected product are obtained in the form of a brown oil.

(g) 1-Bromo-2-ethyl-5-nitrobenzene 25 g (165 mmol) of 4-ethylnitrobenzene are placed in 200 ml of dichloromethane in a round-bottomed flask and under a stream of nitrogen. 20 ml (230 mmol) of trifluoromethanesulfonic acid and 33 g (115 mmol) of 1,3-dibromo-5,5-dimethylhydantoin are added and the reaction medium is stirred for 2 hours at room temperature. Saturated aqueous sodium hydrosulfite solution is then added. The phases are separated and the organic phase is neutralized with aqueous 2M sodium carbonate solution and then washed with water. It is then dried over magnesium sulfate, filtered and evaporated. 35 g (92%) of the expected product are obtained in the form of a yellow oil.

(h) 3-Bromo-4-ethylphenylamine

In a manner similar to that of Example 1(c), by reacting 34 g (148 mmol) of 1-bromo-2-ethyl-5-nitrobenzene with 33 g (591 mmol) of iron, and after purification by chromatography on a column of silica eluted with a mixture of heptane and ethyl acetate (90/10), 27 g (89%) of the expected product are obtained in the form of a yellow oil.

(i) 3-Bromo-4-ethylphenol

In a manner similar to that of Example 1(d), by reacting 27 g (135 mmol) of 3-bromo-4-ethylphenylamine with 11 g (162 mmol) of sodium nitrite, and after purification by chromatography on a column of silica eluted with a mixture of heptane and ethyl acetate (90/10), 13 g (49%) of the expected product are obtained in the form of a brown oil.

(j) 1-Bromo-2-ethyl-5-ethoxymethoxybenzene

In a manner similar to that of Example 1(e), by reacting 13 g (65 mmol) of 3-bromo-4-ethylphenol with 6.7 ml (72 mmol) of methoxyethyl chloride, and after purification by chromatography on a column of silica eluted with a mixture of heptane and ethyl acetate (90/10), 12 g (76%) of the expected product are obtained in the form of a yellow oil.

(k) 2-Ethyl-5-ethoxymethoxyphenylboronic acid 12 g (49 mmol) of 1-bromo-2-ethyl-5-ethoxymethoxybenzene are placed in 200 ml of dry THF in a round-bottomed flask and under a stream of nitrogen. The reaction medium is cooled to −78° C. and 23 ml (58 mmol) of 2.5M n-butyllithium in hexane are added dropwise. 20 minutes later, 13.6 ml (59 mmol) of triisopropyl borate are added slowly. Stirring is continued for 1 hour at −78° C. The mixture is then poured into a solution of water and hydrochloric acid and is then extracted with ethyl acetate. The organic phase is dried over magnesium sulfate, filtered and evaporated. The residue obtained is purified by chromatography on a column of silica eluted with a mixture of heptane and ethyl acetate (50/50). After evaporating off the solvents, 6.7 g (65%) of the expected product are obtained in the form of white crystals.

(l) 1-(5'-Ethoxymethoxy-2,2'-diethylbiphenyl-4-yl)propan-1-one

In a manner similar to that of Example 1(g), by reacting 2 g (8.9 mmol) of 2-ethyl-5-ethoxymethoxyphenylboronic acid with 2.1 g (6.9 mmol) of 2-ethyl-4-propionylphenyl 1,1,1-trifluoromethanesulfonate, a black oil is obtained, which is used without further purification for the rest of the synthesis.

(m) 1-(2,2'-Diethyl-5'-hydroxybiphenyl-4-yl)propan-1-one

In a manner similar to that of Example 1(h), starting with 1-(5'-ethoxymethoxy-2,2'-diethylbiphenyl-4-yl)propan-1-one, and after purification by chromatography on a column of silica eluted with a mixture of heptane and ethyl acetate (50/50), 1.6 g (86%) of the expected product are obtained in the form of a yellow oil.

(n) 1-{5'-[3,4-Bis(benzoyloxymethyl)benzyloxy]-2,2'-diethylbiphenyl-4-yl}-1-propanone In a manner similar to that of Example 1(o), by reacting 1.67 g (5.9 mmol) of 1-(2,2'-diethyl-5'-hydroxybiphenyl-4-yl)-1-propanone with 2.73 g (6.2 mmol) of 3,4-bis(benzoyloxymethyl)benzyl bromide, and after purification by chromatography on a column of silica eluted with a mixture of heptane and ethyl acetate (95/5), 1.88 g (50%) of the expected product are obtained in the form of an oil.

(o) 1-{5'-[3,4-Bis(hydroxymethyl)benzyloxy]-2,2'-diethylbiphenyl-4-yl}-1-propanone In a manner similar to that of Example 1(p), starting with 1.8 g (2.9 mmol) of 1-{5'-[3,4-bis(benzoyloxymethyl)benzyloxy]-2,2'-diethylbiphenyl-4-yl}-1-propanone, and after purification by chromatography on a column of silica eluted with a mixture of heptane and ethyl acetate (40/60), 840 mg (68%) of the expected product are obtained in the form of a colorless oil.

(p) {5-[6,2'-Diethyl-4'-(1-ethyl-1-hydroxypropyl)biphenyl-3-yloxymethyl]-2-hydroxymethyl-phenyl}methanol In a manner similar to that of Example 1(q), by reacting 840 mg (1.9 mmol) of 1-{5'-[3,4-bis(hydroxymethyl)benzyloxy]-2,2'-diethylbiphenyl-4-yl}-1-propanone with 5.2 ml (16 mmol) of ethylmagnesium bromide (3M/ether), and after purification by chromatography on a column of silica eluted with a mixture of heptane and ethyl acetate (40/60), 254 mg (29%) of {5-[6,2'-diethyl-4'-(1-ethyl-1-hydroxypropyl)biphenyl-3-yloxymethyl]-2-hydroxymethylphenyl}methanol are obtained in the form of white crystals with a melting point of 93° C.

EXAMPLE 3

{4-[6-Ethyl-4'-(1-ethyl-1-hydroxypropyl)-2'-propylbiphenyl-3-yloxymethyl]-2-hydroxymethylphenyl}methanol (a) 1-(5'-Ethoxymethoxy-2'-ethyl-2-propylbiphenyl-4-yl)propan-1-one In a manner similar to that of Example 1(g), by reacting 1.58 g (7.1 mmol) of 2-ethyl-5-ethoxymethoxyphenylboronic acid obtained in 2(j) with 1.76 g (5.4 mmol) of 4-propionyl-2-propylphenyl 1,1,1-trifluoromethanesulfonate obtained in 1(b), a brown oil is obtained, which is used without purification.

(b) 1-(2'-Ethyl-5'-hydroxy-2-propylbiphenyl-4-yl)propan-1-one

In a manner similar to that of Example 1(h), starting with 1-(5'-ethoxymethoxy-2'-ethyl-2-propylbiphenyl-4-yl)-1-propanone, and after purification by chromatography on a column of silica eluted with a mixture of heptane and ethyl acetate (90/10), 1.28 g (80%) of the expected product are obtained in the form of an oil.

(c) 1-{5'-[3,4-Bis(benzoyloxymethyl)benzyloxy]-2'-ethyl-2-propylbiphenyl-4-yl}-1-propan-one In a manner similar to that of Example 1(o), by reacting 1.28 g (4.3 mmol) of 1-(2'-ethyl-5'-hydroxy-2-propylbiphenyl-4-yl)-1-propanone with 1.98 g (4.5 mmol) of 3,4-bis(benzoyloxymethyl)benzyl bromide, an oil is obtained, which is used without purification.

(d) 1-{5'-[3,4-Bis(hydroxymethyl)benzyloxy]-2'-ethyl-2-propylbiphenyl-4-yl}-1-propanone In a manner similar to that of Example 1(p), starting with 1-{5'-[3,4-bis(benzoyloxymethyl)benzyloxy]-2'-ethyl-2-propylbiphenyl-4-yl}-1-propanone, and after purification by chromatography on a column of silica eluted with a mixture of heptane and ethyl acetate (30/70), 830 mg (43%) of the expected product are obtained in the form of a colorless oil.

(e) {4-[6-Ethyl-4'-(1-ethyl-1-hydroxypropyl)-2'-propylbiphenyl-3-yloxymethyl]-2-hydroxymethylphenyl}methanol In a manner similar to that of Example 1(q), by reacting 830 mg (1.9 mmol) of 1-{5'-[3,4-bis(hydroxymethyl)benzyloxy]-2'-ethyl-2-propylbiphenyl-4-yl}-1-propanone with 5.1 ml (15.2 mmol) of ethylmagnesium bromide (3M/ ether), and after purification by chromatography on a column of silica eluted with a mixture of heptane and ethyl acetate (40/60), 700 mg (77%) of {4-[6-ethyl-4'-(1-ethyl-1-hydroxypropyl)-2'-propylbiphenyl-3-yloxymethyl]-2-hydroxymethylphenyl}methanol are obtained in the form of white crystals with a melting point of 101° C.

EXAMPLE 4

{4-[6-Ethyl-4'-(1-ethyl-1-hydroxypropyl)-2'-isopropylbiphenyl-3-yloxymethyl]-2-hydroxymethylphenyl}methanol (a) 1-(4-Hydroxy-3-isopropylphenyl)propan-1-one In a manner similar to that of Example 1(a), by reacting 10 g (73 mmol) of 2-isopropylphenol with 6.3 ml (73 mmol) of propionyl chloride, 4.5 g (32%) of the expected product are obtained in the form of white crystals with a melting point of 105° C.

(b) 2-Isopropyl-4-propionylphenyl 1,1,1-trifluoromethanesulfonate

In a manner similar to that of Example 1(b), by reacting 4.5 g (24 mmol) of 1-(4-hydroxy-3-isopropylphenyl)-1-propanone with 4.4 ml (26 mmol) of trifluoromethanesulfonic anhydride, 7.5 g (100%) of the expected product are obtained.

(c) 1-(5'-Ethoxymethoxy-2'-ethyl-2-isopropylbiphenyl-4-yl)propan-1-one

In a manner similar to Example 1(g), by reacting 1.8 g (8 mmol) of 2-ethyl-5-ethoxymethoxyphenylboronic acid obtained in 20) with 2 g (6.2 mmol) of 2-isopropyl-4-propionylphenyl 1,1,1-trifluoromethanesulfonate, a brown oil is obtained, which is used without purification.

(d) 1-(2'-Ethyl-5'-hydroxy-2-isopropylbiphenyl-4-yl)propan-1-one

In a manner similar to that of Example 1(h), starting with 1-(5'-ethoxymethoxy-2'-ethyl-2-isopropylbiphenyl-4-yl)propan-1-one, and after purification by chromatography on a column of silica eluted with a mixture of heptane and ethyl acetate (80/20), 660 mg (35%) of the expected product are obtained in the form of a colorless oil.

(e) 1-{5'-[3,4-Bis(benzoyloxymethyl)benzyloxy]-2'-ethyl-2-isopropylbiphenyl-4-yl}-1-propanone In a manner similar to that of Example 1(o), by reacting 660 mg (2.2 mmol) of 1-(2'-ethyl-5'-hydroxy-2-isopropylbiphenyl-4-yl)propan-1-one with 1 g (2.3 mmol) of 3,4-bis-(benzoyloxymethyl)benzyl bromide, an oil is obtained, which is used without purification.

(f) 1{-5'-[3,4-Bis(hydroxymethyl)benzyloxy]-2'-ethyl-2-isopropylbiphenyl-4-yl}-1-propanone In a manner similar to that of Example 1(p), starting with 1-{5'-[3,4-bis(benzoyloxymethyl)benzyloxy]-2'-ethyl-2-isopropylbiphenyl-4-yl}-1-propanone, and after purification by chromatography on a column of silica eluted with a mixture of heptane and ethyl acetate (50/50), 810 mg (83%) of the expected product are obtained in the form of a colorless oil.

(g) {4-[6-Ethyl-4'-(1-ethyl-1-hydroxypropyl)-2'-isopropylbiphenyl-3-yloxymethyl]-2-hydroxymethylphenyl}methanol In a manner similar to that of Example 1(q), by reacting 810 mg (1.8 mmol) of 1-{5'-[3,4-bis(hydroxymethyl)benzyloxy]-2'-ethyl-2-isopropylbiphenyl-4-yl}-1-propanone with 4.8 ml (15 mmol) of ethylmagnesium bromide (3M/ether), and after purification by chromatography on a column of silica eluted with a mixture of heptane and ethyl acetate (35/65), 600 mg (70%) of {4-[6-Ethyl-4'-(1-ethyl-1-hydroxypropyl)-2'-isopropylbiphenyl-3-yloxymethyl]-2-hydroxymethylphenyl}methanol are obtained in the form of white crystals with a melting point of 109° C.

EXAMPLE 5

{2-[4'-(1-Ethyl-1-hydroxypropyl)-6-methyl-2'-propylbiphenyl-3-yl]ethyl}-2-hydroxymethylphenyl)methanol (a) (3-Bromo-4-methylphenyl)methanol 15 g (70 mmol) of 3-bromo-4-methylbenzoic acid are placed in 150 ml of anhydrous THF in a round-bottomed flask and under a stream of nitrogen. 84 ml of 1M borane/THF are added dropwise and the reaction medium is stirred overnight at room temperature. A THF/water (50/50) solution is added slowly at 0° C. and the mixture is then poured into saturated aqueous ammonium chloride solution and extracted with ethyl acetate. The organic phase is dried over magnesium sulfate, filtered and then evaporated. 14.4 g (100%) of the expected product are obtained in the form of a yellow oil.

(b) 3-Bromo-4-methylbenzaldehyde 14.4 g (72 mmol) of (3-bromo-4-methylphenyl)methanol are placed in 200 ml of dichloromethane in a round-bottomed flask. 62.6 g (72 mmol) of manganese oxide are added and the medium is stirred at room temperature overnight. The mixture is filtered through Celite and the solvent is evaporated off. 11.8 g (85%) of the expected product are obtained in the form of an oil.

(c) 2-(3-Bromo-4-methylphenyl)[1,3]dioxolane 11.8 g (60 mmol) of 3-bromo-4-methylbenzaldehyde are placed in 150 ml of toluene in a round-bottomed flask and under nitrogen. 16.5 ml (300 mmol) of ethylene glycol and 571 mg (3 mmol) of para-toluenesulfonic acid are added. The mixture is refluxed for 36 hours and the water formed is separated out using Dean-Stark apparatus. At room temperature, the reaction medium is poured into saturated aqueous sodium hydrogen carbonate solution and then extracted with ether. The organic phase is dried over magnesium sulfate, filtered and evaporated. 13 g (89%) of the expected product are obtained in the form of a brown oil.

(d) 5-[1,3]Dioxolan-2-yl-2-methylphenylboronic acid

In a manner similar to that of Example 2(k), by reacting 11.1 g (46 mmol) of 2-(3-bromo-4-methylphenyl)[1,3]dioxolane with 12.3 ml (55 mmol) of triisopropyl borate, 6 g (88%) of product are obtained in the form of an oil.

(e) 6-Methyl-4'-propionyl-2'-propylbiphenyl-3-carbaldehyde

In a manner similar to that of Example 1(g), by reacting 2 g (6.2 mmol) of 4-propionyl-2-propylphenyl 1,1,1-trifluoromethanesulfonate with 1.2 g (8 mmol) of 5-[1,3]dioxolan-2-yl-2-methylphenylboronic acid, and after purification by chromatography on a column of silica eluted with a mixture of heptane and ethyl acetate (90/10), 1.42 g (78%) of product are obtained in the form of a pale yellow oil.

(f) Dimethyl 4-bromomethylphthalate 10 g (44.6 mmol) of dimethyl 4-hydroxymethylphthalate obtained in 1(i) are placed in 75 ml of dichloromethane in a round-bottomed flask and under a stream of nitrogen. At 5° C., a solution of 2.1 ml (22 mmol) of phosphorous tribromide is added. 2 hours later, water is added slowly. After separation of the phases by settling, the aqueous phase is extracted with dichloromethane and the organic phases are combined, dried over magnesium sulfate, filtered and then evaporated. 8.8 g (69%) of the expected product are obtained in the form of a yellow oil.

(g) Dimethyl 4-(diethoxyphosphorylmethyl)phthalate 65.7 g (229 mmol) of dimethyl 4-bromomethylphthalate are placed in 100 ml (583 mmol) of triethyl phosphite in a round-bottomed flask. The mixture is refluxed for 4 hours. The medium is then distilled to remove the triethyl phosphite. 60.7 g (77%) of the expected product are obtained in the form of a yellow oil.

(h) Dimethyl 4-[(Z)-2-(6-methyl-4'-propionyl-2'-propylbiphenyl-3-yl)vinyl]phthalate 2 g (6 mmol) of dimethyl 4-(diethoxyphosphorylmethyl)phthalate are placed in 50 ml of THF in a round-bottomed flask and under a stream of nitrogen. 3 ml of lithium diisopropylamide (2M/THF) are added, followed by addition of 1.42 g (5 mmol) of 6-methyl-4'-propionyl-2'-propylbiphenyl-3-carbaldehyde. Stirring is continued for 3 days at room temperature. The reaction medium is then poured into water and extracted with ethyl acetate. The organic phase is dried over magnesium sulfate, filtered and then evaporated. The residue obtained is purified by chromatography on a column of silica eluted with a mixture of heptane and ethyl acetate (90/10). After evaporating off the solvents, 900 mg (39%) of the expected product are obtained in the form of a yellow oil.

(i) Dimethyl4-{(Z)-2-[4'-(2-ethyl[1,3]dioxolan-2-yl)-6-methyl-2'-propylbiphenyl-3-yl]vinyl}-phthalate In a manner similar to that of Example 6(c), starting with 900 mg (1.9 mmol) of dimethyl 4-[(Z)-2-(6-methyl-4'-propionyl-2'-propylbiphenyl-3-yl)vinyl]phthalate, 700 mg (70%) of the expected product are obtained in the form of a yellow oil.

(j) Dimethyl 4-{2-[4'(2-ethyl[1,3]dioxolan-2-yl) -6-methyl-2'-propylbiphenyl-3yl]ethyl}-phthalate 700 mg (1.3 mmol) of dimethyl 4-{(Z)-2-[4'-(2-ethyl[1,3]dioxolan-2-yl)-6-methyl-2'-propylbiphenyl-3-yl] vinyl}phthalate are placed in 15 ml of methanol, 15 ml of ethyl acetate and 1 ml of triethylamine in a reactor. The reaction medium is degassed and 100 mg of palladium-on-charcoal (10%) and hydrogen to a pressure of 3.5 bar at 80° C. are added. The reaction medium is filtered and evaporated to give 640 mg (93%) of the expected product in the form of an oil.

(k) (4-{2-[4'(2-Ethyl[1,3]dioxolan-2-yl)-6-methyl-2'-propylbiphenyl-3-yl]ethyl}-2-hydroxymethylphenyl) methanol 182 mg (4.8 mmol) of lithium aluminum hydride are placed in 20 ml of dry THF in a round-bottomed flask and under nitrogen. At 0° C., a solution of 640 mg (1.2 mmol) of dimethyl 4-{2-[4'-(2-ethyl[1,3]dioxolan-2-yl)-6-methyl-2'-propylbiphenyl-3-yl]ethyl}phthalate in 5 ml of THF is added dropwise. The reaction medium is stirred for 1 hour at room temperature. 200 µl of water are then added very slowly, followed by addition of 200 µl of 15% sodium hydroxide solution and then 600 µl of water. The medium is filtered and the filtrate is evaporated to dryness. 640 mg (100%) of the expected product are obtained in the form of a colorless oil.

(l) 1-{5'-[2-(3,4-Bis(hydroxymethyl)phenyl)ethyl]-2'-methyl-2-propylbiphenyl-4-yl}propan-1-one 640 mg (1.4 mmol) of (4-{2-[4'-(2-ethyl[1,3]dioxolan-2-yl)-6-methyl-2'-propylbiphenyl-3-yl]ethyl}-2-hydroxymethylphenyl)methanol are placed in 15 ml of acetone and 15 ml of water in a round-bottomed flask. A spatula-tip of p-toluenesulfonic acid is added and the solution is refluxed for 2 hours 30 minutes. At room temperature, it is poured into saturated aqueous sodium hydrogen carbonate solution and extracted with ethyl acetate. The organic phase is dried over magnesium sulfate, filtered and then evaporated. The residue obtained is purified by chromatography on a column of silica eluted with a mixture of heptane and ethyl acetate (30/70). 300 mg (50%) of the expected product are obtained in the form of a colorless oil.

(m) (4-{2-[4'-(1-Ethyl-1-hydroxypropyl)-6-methyl-2'-propylbiphenyl-3-yl]ethyl}-2-hydroxymethylphenyl) methanol In a manner similar to that of Example 1(q), by reacting 300 mg (0.7 mmol) of 1-{5'-[2-(3,4-bis(hydroxymethyl) phenyl)ethyl]-2'-methyl-2-propylbiphenyl-4-yl}propan-1-one with 1.9 ml (5.6 mmol) of ethylmagnesium bromide (3M/ether), and after purification on a column of silica eluted with a mixture of heptane and ethyl acetate (40/60), 180 mg (56%) of (4-{2-[4'-(1-ethyl-1-hydroxypropyl)-6-methyl-2'-propylbiphenyl-3-yl]ethyl}-2-hydroxymethylphenyl)methanol are obtained in the form of white crystals with a melting point of 76° C.

EXAMPLE 6

(4-{[4'-(1-Ethyl-1-hydroxypropyl)-6,2'-dimethylbiphenyl-3-ylamino]-methyl}-2-hydroxymethylphenyl)methanol (a) 1-(4-Bromo-3-methylphenyl)propan-1-one 24.7 g (126 mmol) of 4-bromo-3-methylbenzonitrile are dissolved in 400 ml of anhydrous dioxane and the medium is then cooled to 0° C. 124 ml (372 mmol) of ethylmagnesium bromide are added dropwise and the medium is then warmed to room temperature and stirred for 4 hours. The reaction medium is treated with 250 ml of 3N HCl and then extracted with a water/ether mixture. A white solid is obtained after trituration from heptane (m=14.5 g, Y=52%).

(b) 2-(4-Bromo-3-methylphenyl)-2-ethyl[1,3]dioxolane 13 g (57 mmol) of 1-(4-bromo-3-methylphenyl)-1-propanone are dissolved in 130 ml of toluene. 54 ml (800 mmol) of ethylene glycol are added, followed by addition of 1.4 g (7.4 mmol) of para-toluenesulfonic acid. The medium is equipped with a distillation assembly of Dean-Stark type and heated at 125° C. for 14 hours. After treatment with dilute sodium hydroxide solution, the organic phase is washed with water and concentrated under reduced pressure. A yellow oil is obtained (m=13.6 g, Y=88%).

(c) 2-Methyl-4-propionylbenzeneboronic acid 1.6 g (65 mmol) of magnesium are suspended in 5 ml of THF and 0.5 ml of 1,2-dibromoethane. One crystal of iodine is added. A solution of 13.6 g (50 mmol) of 2-(4-bromo-3-methylphenyl)-2-ethyl[1,3]dioxolane and 0.4 ml of 1,2-dibromoethane in 70 ml of THF is added slowly. The medium is refluxed for 45 minutes after the end of the addition and then cooled to −78° C. 6.2 ml (55 mmol) of trimethyl borate are added and the medium is maintained at this temperature for 45 minutes. 100 ml of 1N HCl are then added and the medium is warmed to room temperature. After separation of the phases by settling and concentration of the organic phase, the residue obtained is triturated from heptane: a beige-colored solid is obtained (m=5.1 g, Y=54%).

(d) 1-(2,2'-Dimethyl-5'-nitrobiphenyl-4-yl)propan-1-one 2.5 g (13 mmol) of 2-methyl-4-propionylbenzeneboronic acid are placed in 100 ml of dimethoxyethane in a round-bottomed flask, and 2.2 g (10 mmol) of 2-bromo-4-nitrotoluene and 13 ml of aqueous 2M potassium carbonate solution are added. The medium is degassed for 10 minutes with a flow of nitrogen, and 580 mg (0.5 mmol) of tetrakis (triphenylphosphine)palladium are then added. The medium is stirred for 14 hours at 90° C. and then worked up as usual. The residue is obtained after chromatography on a column of silica (eluent: 1 ethyl acetate/9 heptane) to give 2.3 g (81%) of the expected product in the form of a yellow oil.

(e) 1-(5'-Amino-2,2'-dimethylbiphenyl-4-yl)propan-1-one 2.2 g (7.8 mmol) of 1-(2,2'-dimethyl-5'-nitrobiphenyl-4-yl)-1-propanone are dissolved in a mixture of 80 ml of ethanol and 40 ml of water and 10 ml of acetic acid. The mixture is refluxed while 1.7 g (31 mmol) of iron powder are added. The medium is heated for 1 hour and then treated by addition of aqueous ammonia, cooled and filtered through Celite. The solution obtained is diluted in ethyl acetate and then washed with water, and the organic phase is dried and concentrated under reduced pressure. After chromatography on a column of silica (eluent: 60 heptane/40 ethyl acetate), a yellow oil is obtained (m=1.9 g; Y=96%).

(f) Tert-butyl (6,2'-dimethyl-4'propionylbiphenyl-3-yl) carbamate 800 mg (3.15 mmol) of 1-(5'-amino-2,2'-dimethylbiphenyl-4-yl)-1-propanone are dissolved in 50 ml of dichloromethane. 500 µl (3.5 mmol) of triethylamine are added, followed by addition of 760 mg (3.5 mmol) of di-tert-butyl dicarbonate. The medium is stirred at room temperature for 12 hours and then for 2 hours at 50° C. The medium is treated with water and the residue is then purified by chromatography on a column of silica (eluent: 3 heptane/1 ethyl acetate) to give a yellow crystalline solid (m.p. 119° C., m=1.05 g, Y=94%).

(g) 2-Benzoyloxymethyl-5-{[tert-butoxycarbonyl(6,2'-dimethyl-4'-propionylbiphenyl-3-yl)-amino]methyl}benzyl benzoate 900 mg (2.5 mmol) of tert-butyl(6,2'-dimethyl-4'-propionylbiphenyl-3-yl)carbamate are dissolved in 30 ml of dimethylformamide. 110 mg (2.8 mmol) of 60% sodium hydride are added and the medium is stirred for 15 minutes. 1.23 g (2.8 mmol) of 3,4-bis(benzoyloxymethyl)benzyl bromide are then added and the medium is stirred for 12 hours at room temperature. After the usual work-up, the residue obtained is purified by chromatography on a column of silica (eluent: 8 heptane/2 ethyl acetate). A colorless oil is obtained (m=1 g, Y=55%).

(h) 2-Benzoyloxymethyl-5-[(6,2'-dimethyl-4'-propionylbiphenyl-3-ylamino)methyl]benzyl benzoate 1 g (1.4 mmol) of 2-benzoyloxymethyl-5-{[tert-butoxycarbonyl(6,2'-dimethyl-4'-propionyl-biphenyl-3-yl)amino]methyl}benzyl benzoate are dissolved in 50 ml of dichloromethane. 1,1 ml (14 mmol) of trifluoroacetic acid are added and the medium is stirred at room temperature for 6 hours. After extraction with water/dichloromethane, the desired product is obtained in the form of a yellowish oil (m=820 mg, Y=95%).

(i) 1-{5'-[3,4-Bis(hydroxymethyl)benzylamino]-2,2'-dimethylbiphenyl-4-yl}-1-propanone 800 mg (1.3 mmol) of 2-benzoyloxymethyl-5-[(6,2'-dimethyl-4'-propionylbiphenyl-3-ylamino)methyl]benzyl benzoate are dissolved in methanolic 2% potassium carbonate solution and the medium is stirred for 1 hour. After water/dichloromethane extraction, the residue obtained is purified by chromatography on silica gel (eluent: 30 heptane/70 ethyl acetate). A yellow oil is obtained (m=470 mg, Y=88%).

(j) (4-{[4'-(1-Ethyl-1-hydroxypropyl)-6,2'-dimethylbiphenyl-3-ylamino]methyl}-2-hydroxymethylphenyl)methanol 450 mg (1.1 mmol) of 1-{5'-[3,4-bis(hydroxymethyl)benzylamino]-2,2'-dimethylbiphenyl-4-yl}-1-propanone are dissolved in 30 ml of THF. 1.5 ml (4.5 mmol) of ethylmagnesium bromide are added and the medium is stirred at room temperature for 1 hour. After the usual work-up, the residue is purified by chromatography on silica gel (eluent: 1 heptane/1 ethyl acetate). A white solid is obtained (m=130 mg; Y=27%).

$^1$H NMR (CDCl$_3$): 0.80 (t, 6H, J =7.4 Hz); 1.85 (q, 4H, J=7.5 Hz); 1.91 (s, 3H); 2.06 (s, 3H); 2.86 (bs, 2H); 4.30 (s, 2H); 4.72 (s, 2H); 4.73 (s, 2H); 6.45 (d, 1H, J=2.4 Hz); 6.55 (dd, 1H, J1=2.4 Hz, J2=8.1 Hz); 7.04 (m, 2H); 7.15 (m, 1H); 7.24–7.37 (m, 4H).

EXAMPLE 7

Formulations

1) Oral Route (a) The following composition is prepared in the form of a 0.2 g tablet

| | |
|---|---|
| Compound of Example 2 | 0.005 g |
| Pregelatinized starch | 0.065 g |
| Microcrystalline cellulose | 0.075 g |
| Lactose | 0.050 g |
| Magnesium stearate | 0.005 g |

For the treatment of ichthyosis, 1 to 3 tablets per day are administered to an adult individual for 1 to 12 months depending on the seriousness of the case treated.

(b) A drinkable suspension intended to be packaged in 5 ml ampules is prepared.

| | | |
|---|---|---|
| Compound of Example 6 | | 0.050 mg |
| Glycerol | | 0.500 g |
| 70% sorbitol | | 0.500 g |
| Sodium saccharinate | | 0.010 g |
| Methyl para-hydroxybenzoate | | 0.040 g |
| Flavouring | q.s. | |
| Purified water | q.s | 5 ml |

For the treatment of acne, 1 ampule per day is administered to an adult individual for 1 to 12 months depending on the seriousness of the case treated.

(c) The following formulation intended to be packaged in gel capsules is prepared:

| | | |
|---|---|---|
| Compound of Example 5 | | 0.0001 mg |
| Corn starch | | 0.060 g |
| Lactose | q.s. | 0.300 g |

The gel capsules used consist of gelatin, titanium oxide and a preserving agent. In the treatment of psoriasis, 1 gel capsule per day is administered to an adult individual for 1 to 12 months.

(d) The following formulation intended to be packaged in gel capsules is prepared:

| | | |
|---|---|---|
| Compound of Example 1 | | 0.02 mg |
| Cyclosporin | | 0.050 g |
| Corn starch | | 0.060 g |
| Lactose | q.s. | 0.300 g |

The gel capsules used consist of gelatin, titanium oxide and a preserving agent. In the treatment of psoriasis, 1 gel capsule per day is administered to an adult individual for 1 to 12 months.

2) Topical Route (a) The nonionic water-in-oil cream below is prepared:

| | |
|---|---|
| Compound of Example 5 | 0.100 g |
| Mixture of emulsifying lanolin alcohols, waxes and refined oils, sold by the company Beiersdorf under the name "Anhydrous eucerin" | 39.900 g |
| Methyl para-hydroxybenzoate | 0.075 g |

-continued

| | | |
|---|---|---|
| Propyl para-hydroxybenzoate | | 0.075 g |
| Sterile demineralized water | q.s. | 100.000 g |

This cream is applied to skin afflicted with psoriasis 1 to 2 times a day for 1 to 12 months.

(b) A gel is prepared by preparing the formulation below:

| | | |
|---|---|---|
| Compound of Example 2 | | 0.001 g |
| Erythromycin base | | 4.000 g |
| Butylhydroxytoluene | | 0.050 g |
| Hydroxypropylcellulose sold by the company Hercules under the name "Klucel HF" | | 2.000 g |
| Ethanol (at 95°) | q.s | 100.000 g |

This gel is applied to skin afflicted with dermatitis or with acne 1 to 3 times a day for 6 to 12 weeks depending on the severity of the case treated.

(c) An antiseborrhoeic lotion is prepared by mixing together the following ingredients:

| | | |
|---|---|---|
| Compound of Example 1 | | 0.030 g |
| Propylene glycol | | 5.000 g |
| Butylhydroxytoluene | | 0.100 g |
| Ethanol (at 95°) | q.s | 100.000 g |

This lotion is applied twice a day to a seborrhoeic scalp and a significant improvement is observed within a period of 2 to 6 weeks.

(d) A cosmetic composition to combat the harmful effects of sunlight is prepared by mixing together the following ingredients:

| | | |
|---|---|---|
| Compound of Example 3 | | 1.000 g |
| Benzylidenecamphor | | 4.000 g |
| Fatty acid triglycerides | | 31.000 g |
| Glyceryl monostearate | | 6.000 g |
| Stearic acid | | 2.000 g |
| Cetyl alcohol | | 1.200 g |
| Lanolin | | 4.000 g |
| Preserving agents | | 0.300 g |
| Propylene glycol | | 2.000 g |
| Triethanolamine | | 0.500 g |
| Fragrance | | 0.400 g |
| Demineralized water | q.s | 100.000 g |

This composition is applied daily and helps to combat photo-induced aging.

(e) The oil-in-water cream below is prepared:

| | | |
|---|---|---|
| Compound of Example 5 | | 0.500 g |
| Retinoic acid | | 0.020 g |
| Cetyl alcohol | | 4.000 g |
| Glyceryl monostearate | | 2.500 g |
| PEG-50 stearate | | 2.500 g |
| Karite butter | | 9.200 g |
| Propylene glycol | | 2.000 g |
| Methyl para-hydroxybenzoate | | 0.075 g |
| Propyl para-hydroxybenzoate | | 0.075 g |
| Sterile demineralized water | q.s. | 100.000 g |

This cream is applied to skin afflicted with psoriasis 1 to 2 times a day for 30 days for an attacking treatment, and indefinitely for a maintenance treatment.

(f) A topical gel is prepared by mixing together the following ingredients:

| | | |
|---|---|---|
| Compound of Example 2 | | 0.050 g |
| Ethanol | | 43.000 g |
| α-Tocopherol | | 0.050 g |
| Carboxyvinyl polymer sold under the name "Carbopol 941" by the company "Goodrich" | | 0.500 g |
| Triethanolamine as an aqueous solution at 20% by weight | | 3.800 g |
| Water | | 9.300 g |
| Propylene glycol | q.s. | 100.000 g |

This gel is applied in the treatment of acne 1 to 3 times a day for 6 to 12 weeks depending on the severity of the case treated.

(g) A lotion for preventing hair loss and for promoting regrowth of the hair is prepared by mixing together the following ingredients:

| | | |
|---|---|---|
| Compound of Example 4 | | 0.05 g |
| Compound sold under the name "Minoxidil" | | 1.00 g |
| Propylene glycol | | 20.00 g |
| Ethanol | | 34.92 g |
| Polyethylene glycol (molecular mass = 400) | | 40.00 g |
| Butylhydroxyanisole | | 0.01 g |
| Butylhydroxytoluene | | 0.02 g |
| Water | q.s. | 100.00 g |

This lotion is applied 1 to 2 times a day for 3 months to a scalp which has suffered hair loss, and indefinitely for a maintenance treatment.

(h) An anti-acne cream is prepared by mixing together the following ingredients:

| | | |
|---|---|---|
| Compound of Example 6 | | 0.050 g |
| Retinoic acid | | 0.010 g |
| Mixture of glyceryl stearate and polyethylene glycol stearate (75 mol) sold under the name "Gelot 64" by the company "Gattefosse" | | 15.000 g |
| Polyoxyethylenated kernel oil containing 6 mol of ethylene oxide, sold under the name "Labrafil M2130 CS" by the company "Gattefosse" | | 8.000 g |
| Perhydrosqualene | | 10.000 g |
| Preserving agents | q.s. | |
| Polyethylene glycol (molecular mass = 400) | | 8.000 g |
| Disodium salt of ethylenediamine tetraacetic acid | | 0.050 g |
| Purified water | q.s | 100.000 g |

This cream is applied to skin afflicted with dermatitis or acne 1 to 3 times a day for 6 to 12 weeks.

(i) An oil-in-water cream is prepared by preparing the following formulation:

| | | |
|---|---|---|
| Compound of Example 2 | | 0.020 g |
| Betamethasone 17-valerate | | 0.050 g |
| S-carboxymethylcysteine | | 3.000 g |
| Polyoxyethylene stearate (40 mol of ethylene oxide) sold under the name "Myrj 52" by the company "Atlas" | | 4.000 g |
| Sorbitan monolaurate polyoxyethylenated with 20 mol of ethylene oxide, sold under the name "Tween 20" by the company "Atlas" | | 1.800 g |
| Mixture of glyceryl mono- and distearate sold under the name "Géléol" by the | | 4.200 g |

-continued

| | | |
|---|---|---|
| company "Gattefosse" | | |
| Propylene glycol | | 10.000 g |
| Butylhydroxyanisole | | 0.010 g |
| Butylhydroxytoluene | | 0.020 g |
| Cetostearyl alcohol | | 6.200 g |
| Preserving agents | q.s. | |
| Perhydrosqualene | | 18.000 g |
| Mixture of caprylic/capric triglycerides sold under the name "Miglyol 812" by the company "Dynamit Nobel" | | 4.000 g |
| Triethanolamine (99% by weight) | | 2.500 g |
| Water | q.s. | 100.000 g |

This is cream is applied twice a day to skin afflicted with inflammatory dermatitis, for 30 days.

(j) The oil-in-water cream below is prepared:

| | | |
|---|---|---|
| Lactic acid | | 5.000 g |
| Compound of Example 1 | | 0.020 g |
| Polyoxyethylene stearate (40 mol of ethylene oxide) sold under the name "Myrj 52" by the company "Atlas" | | 4.000 g |
| Sorbitan monolaurate polyoxyethylenated with 20 mol of ethylene oxide, sold under the name "Tween 20" by the company "Atlas" | | 1.800 g |
| Mixture of glyceryl mono- and distearate sold under the name "Geleol" by the company "Gattefosse" | | 4.200 g |
| Propylene glycol | | 10.000 g |
| Butylhydroxyanisole | | 0.010 g |
| Butylhydroxytoluene | | 0.020 g |
| Cetostearyl alcohol | | 6.200 g |
| Preserving agents | q.s. | |
| Perhydrosqualene | | 18.000 g |
| Mixture of caprylic/capric triglycerides sold under the name "Miglyol 812" by the company "Dynamit Nobel" | | 4.000 g |
| Water | q.s. | 100.000 g |

This cream is applied once a day, and helps to combat aging, whether photo-induced or chronological.

(k) The anhydrous ointment below is prepared:

| | | |
|---|---|---|
| Compound of Example 5 | | 5.000 g |
| Liquid petroleum jelly | | 50.00 g |
| Butylhydroxytoluene | | 0.050 g |
| White petroleum jelly | q.s. | 100 g |

This ointment is applied twice a day for 30 days to skin afflicted with squamous dermatitis.

3) Intralesional Route (a) The following composition is prepared:

| | | |
|---|---|---|
| Compound of Example 1 | | 0.002 g |
| Ethyl oleate | q.s. | 10 g |

In the treatment of malignant melanoma, the composition is injected into an adult individual at a frequency of 1 to 7 times a week for 1 to 12 months.

(b) The following composition is prepared:

| | | |
|---|---|---|
| Compound of Example 2 | | 0.050 g |
| Olive oil | q.s. | 2 g |

In the treatment of basocellular carcinoma, the composition is injected into an adult individual at a frequency of 1 to 7 times a week for 1 to 12 months.

(c) The following composition is prepared:

| | | |
|---|---|---|
| Compound of Example 3 | | 0.1 mg |
| Sesame oil | q.s. | 2 g |

In the treatment of spinocellular carcinoma, the composition is injected into an adult individual at a frequency of 1 to 7 times a week for 1 to 12 months.

(d) The following composition is prepared:

| | | |
|---|---|---|
| Compound of Example 4 | | 0.001 mg |
| Methyl benzoate | q.s. | 10 g |

In the treatment of carcinoma of the colon, the composition is injected into an adult individual at a frequency of 1 to 7 times a week for 1 to 12 months.

4) Intravenous Route (a) The injectable lipid emulsion below is prepared:

| | | |
|---|---|---|
| Compound of Example 5 | | 0.001 mg |
| Soyabean oil | | 10.000 g |
| Egg phospholipid | | 1.200 g |
| Glycerol | | 2.500 g |
| Water for injection | q.s | 100.000 g |

In the treatment of psoriasis, the composition is injected into an adult individual at a frequency of 1 to 7 times a week for 1 to 12 months.

(b) The injectable lipid emulsion below is prepared:

| | | |
|---|---|---|
| Compound of Example 6 | | 0.010 g |
| Cotton oil | | 10.000 g |
| Soyabean lecithin | | 0.750 g |
| Sorbitol | | 5.000 g |
| DL, α-tocopherol | | 0.100 g |
| Water for injection | q.s | 100.000 g |

In the treatment of ichthyosis, the composition is injected into an adult individual at a frequency of 1 to 7 times a week for 1 to 12 months.

(c) The injectable lipid emulsion below is prepared:

| | | |
|---|---|---|
| Compound of Example 1 | | 0.001 g |
| Soyabean oil | | 15.000 g |
| Acetylated monoglycerides | | 10.000 g |
| Pluronic F-108 | | 1.000 g |
| Glycerol | | 2.500 g |
| Water for injection | q.s | 100.000 g |

In the treatment of leukaemia, the composition is injected into an adult individual at a frequency of 1 to 7 times a week for 1 to 12 months.

(d) The mixed micellar composition below is prepared:

| | | |
|---|---|---|
| Compound of Example 2 | | 0.001 g |
| Lecithin | | 16.930 g |
| Glycocholic acid | | 8.850 g |
| Water for injection | q.s | 100.000 g |

In the treatment of malignant melanoma, the composition is injected into an adult individual at a frequency of 1 to 7 times a week for 1 to 12 months.

(e) The cyclodextrin composition below is prepared:

| | | |
|---|---|---|
| Compound of Example 5 | | 0.1 mg |
| β-Cyclodextrin | | 0.100 g |
| Water for injection | q.s | 10.000 g |

In the treatment of graft rejection, the composition is injected into an adult individual at a frequency of 1 to 7 times a week for 1 to 12 months.

(f) The cyclodextrin composition below is prepared:

| | | |
|---|---|---|
| Compound of Example 3 | | 0.010 g |
| 2-Hydroxypropyl-β-cyclodextrin | | 0.100 g |
| Water for injection | q.s | 10.000 g |

In the treatment of cancer of the kidney, the composition is injected into an adult individual at a frequency of 1 to 7 times a week for 1 to 12 months.

EXAMPLE 8

Tests to Evaluate the Biological Activity of the Compounds of the Invention—Activity on the Differentiation of HL60 Cells Calcitrol induces the differentiation of promyelocytic leukaemia cells (HL60) into monocytes/macrophages. This differentiation-inductive effect is a well-characterized marker of cellular vitamin D. One of the most important antimicrobial products of macrophages is hydrogen peroxide, which may be analysed experimentally by the reduction of NBT (Nitroblue Tetrazolium).

The method used is as follows: the HL60 cells are inoculated into 6-well plates and then treated immediately with a test compound. After culturing for 4 days, the cells are incubated with phorbol TPA ester and NBT for a short period and the differentiated cells, i.e., the ones that are positive to NBT, are counted.

The differentiation-inductive effect on HL60 cells of the compounds according to the invention and also that of the reference compound, calcitriol, are given in Table I. The results show that the compounds of Examples 1 to 4 have differentiation-inducing activity on HL60 cells similar to that of calcitriol, the compound of Example 5 even having markedly superior activity.

As regards the compound of Example 6, it shows less good activity compared with calcitriol, but nevertheless remains a very advantageous compound when compared with the compounds of the prior art.

TABLE I

| TEST COMPOUND | AC50-HL60 (in nM) |
|---|---|
| Calcitriol | 10.7 |
| Compound of Example 1 | 7.6 |
| Compound of Example 2 | 15.0 |
| Compound of Example 3 | 11.0 |
| Compound of Example 4 | 27.0 |
| Compound of Example 5 | 1.8 |
| Compound of Example 6 | 147 |

EXAMPLE 9

Tests to Evaluate the Biological Activity of the Compounds of the Invention—Measurement of the VDR Agonist Activity (AC50 hVDR)

The VDR agonist activity of the compounds of the invention may be tested on the HeLa cell line by cotransfection of the expression vector of the human VDR receptor and of the reporter plasmid p240Hase-CAT which contains the region −1399 to +76 of rat 24-hydroxylase promoter, cloned upstream of the coding phase of the chloramphenicol-acetyltransferase (CAT) gene. 18 hours after cotransfection, the test compound is added to the medium. After treatment for 18 hours, the CAT activity of the cell lysates is assayed by means of an ELISA test (Enzyme Linked ImmunoSorbent Assay, sold by Roche Molecular Biochemicals). The agonist activity may be characterized in this system of cotransfection by determining the dose required to achieve 50% of the maximum activity of the test compound (AC50).

The measurement of the VDR agonist activity of the compounds according to the invention and also that of the reference compound, calcitriol, are given in Table II.

These results show that the compounds according to the present invention have activities that are comparable to that of calcitriol, the compound of Example 5 having, in this case also, superior activity.

These results once again show that the compound of Example 6 shows less good activity compared with calcitriol, but nevertheless remains a very advantageous compound when compared with the compounds of the prior art.

TABLE II

| TEST COMPOUND | AC50-hVDR (in nM) |
|---|---|
| Calcitriol | 2.5 |
| Compound of Example 1 | 2.4 |
| Compound of Example 2 | 4.1 |
| Compound of Example 3 | 2.2 |
| Compound of Example 4 | 3.2 |
| Compound of Example 5 | 0.6 |
| Compound of Example 6 | 50 |

EXAMPLE 10

Tests to Evaluate the Biological Activity of the Compounds of the Invention—Activity on the Proliferation of Human Keratinocytes It is known that 1,25-dihydroxyvitamin D3, known as calcitriol and corresponding to natural vitamin D, inhibits the proliferation of human keratinocytes in culture.

The method used is as follows: normal human keratinocytes are inoculated at low density into a 24-well plate. After 4 hours, the test compounds are added to the culture medium. After culturing for 5 days, the proliferation of the keratinocytes is determined by incorporating 5-bromo-2′- deoxyuridine (BrdU) into the DNA. The amount of BrdU incorporated is then measured using the ELISA test (Enzyme Linked ImmunoSorbent Assay, sold by Roche Molecular Biochemicals).

The inhibitory effect on keratinocyte proliferation of the compounds according to the invention and of calcitriol used as reference compound is summarized in Table III. The IC50 value indicates the concentration of the test compound for which the compound inhibits the proliferation of the keratinocytes by 50%.

These results make it possible to show that the compounds of the invention have inhibitory activity on keratinocyte proliferation in the same ranges of values as calcitriol; the compound of Example 5 is distinguished by an activity more than 5 times greater than that of calcitriol.

As regards the compound of Example 6, it shows less good activity compared with calcitriol, but nevertheless remains a very advantageous compound when compared with the compounds of the prior art.

TABLE III

| MEASURED ACTIVITY | IC50-proliferation of KHNs (in nM) |
|---|---|
| Calcitriol | 15.3 |
| Compound of Example 1 | 16.0 |
| Compound of Example 2 | 53.0 |
| Compound of Example 3 | 15.0 |
| Compound of Example 4 | 26.0 |
| Compound of Example 5 | 2.4 |
| Compound of Example 6 | 122 |

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A triaromatic vitamin D analogue having the structural formula (I) below:

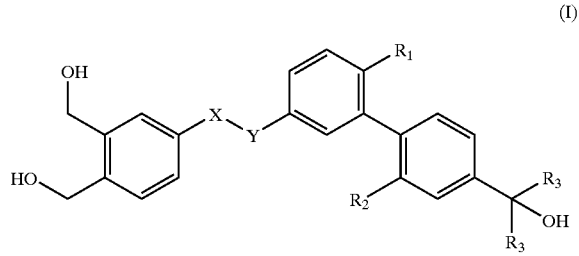

(I)

in which:
- X—Y represents the following structural bonds:
- —$CH_2$—$CH_2$—
- —$CH_2$—O—
- —O—$CH_2$—
- —$CH_2$—N($R_4$)—

$R_4$ having the meanings given below,
- $R_1$ represents a methyl radical or an ethyl radical,
- $R_2$ represents an ethyl radical, a propyl radical or an isopropyl radical,
- $R_3$ represents an ethyl radical or a trifluoromethyl radical,
- $R_4$ represents a hydrogen atom, a methyl radical, an ethyl radical or a propyl radical, optical and geometrical isomers of the compounds of formula (I), and salts thereof.

2. The vitamin D analogue as defined by claim 1, in the form of a salt of a mineral or organic acid.

3. A triaromatic vitamin D analogue is selected from the group consisting of:
{5-[4'-(1-Ethyl-1-hydroxypropyl)-6-methyl-2'-propylbiphenyl-3-yloxymethyl]-2-hydroxymethylphenyl}methanol;
{5-[6,2'-Diethyl-4'-(1-ethyl-1-hydroxypropyl)biphenyl-3-yloxymethyl]-2-hydroxymethyl-phenyl}methanol;
{4-[6-Ethyl-4'-(1-ethyl-1-hydroxypropyl)-2'-propylbiphenyl-3-yloxymethyl]-2-hydroxymethylphenyl}methanol;
{4-[6-Ethyl-4'-(1-ethyl-1-hydroxypropyl)-2'-isopropylbiphenyl-3-yloxymethyl]-2-hydroxymethylphenyl}methanol;
(4-{2-[4'-(1-Ethyl-1-hydroxypropyl)-6-methyl-2'-propylbiphenyl-3-yl]ethyl}-2-hydroxymethylphenyl)methanol;
{4-[4'-(1-Ethyl-1-hydroxypropyl)-6-methyl-2'-propylbiphenyl-3-ylmethoxy]-2-hydroxymethylphenyl}methanol;
(4-{[4'-(1-Ethyl-1-hydroxypropyl)-6-methyl-2'-propylbiphenyl-3-ylamino]methyl}-2-hydroxymethylphenyl)methanol;
[4-({[4'-(1-Ethyl-1-hydroxypropyl)-6-methyl-2'-propylbiphenyl-3-yl]methylamino}methyl)-2-hydroxymethylphenyl]methanol;
[4-({Ethyl-[4'-(1-ethyl-1-hydroxypropyl)-6-methyl-2'-propylbiphenyl-3-yl]amino}methyl)-2-hydroxymethylphenyl]methanol;
[4-({[4'-(1-Ethyl-1-hydroxypropyl)-6-methyl-2'-propylbiphenyl-3-yl]propylamino}methyl)-2-hydroxymethylphenyl]methanol;
(2-Hydroxymethyl-4-{2-[6-methyl-2'-propyl-4'-(2,2,2-trifluoro-1-hydroxy-1trifluoromethyl-ethyl)biphenyl-3-yl]ethyl}phenyl)methanol;
{2-Hydroxymethyl-4-[6-methyl-2'-propyl-4'-(2,2,2-trifluoro-1-hydroxy-1-trifluoromethyl-ethyl)biphenyl-3-yloxymethyl]phenyl}methanol;
{2-Hydroxymethyl-4-[6-methyl-2'-propyl-4'-(2,2,2-trifluoro-1-hydroxy-1-trifluoromethyl-ethyl)biphenyl-3-ylmethoxy]phenyl}methanol;
(2-Hydroxymethyl-4-{[6-methyl-2'-propyl-4'-(2,2,2-trifluoro-1-hydroxy-1-trifluoromethyl-ethyl)biphenyl-3-ylamino]methyl}phenyl)methanol;
[2-Hydroxymethyl-4-({N-methyl[6-methyl-2'-propyl-4'-(2,2,2-trifluoro-1-hydroxy-1-trifluoromethyl-ethyl)biphenyl-3-yl]amino}methyl)phenyl]methanol;
[4-({N-Ethyl[6-methyl-2'-propyl-4'-(2,2,2-trifluoro-1-hydroxy-1-trifluoromethyl-ethyl)biphenyl-3-yl]amino}methyl)-2-hydroxymethylphenyl]methanol;
[2-Hydroxymethyl-4-({[6-methyl-2'-propyl-4'-(2,2,2-trifluoro-1-hydroxy-1-trifluoromethyl-ethyl)biphenyl-3-yl]N-propyl-amino}methyl)phenyl]methanol;
(4-{2-[6-Ethyl-4'-(1-ethyl-1-hydroxypropyl)-2'-propylbiphenyl-3-yl]ethyl}-2-hydroxy-methylphenyl)methanol;
{4-[6-Ethyl-4'-(1-ethyl-1-hydroxypropyl)-2'-propylbiphenyl-3-ylmethoxy]-2-hydroxy-methylphenyl}methanol;
(4-{[6-Ethyl-4'-(1-ethyl-1-hydroxypropyl)-2'-propylbiphenyl-3-ylamino]methyl}-2-hydroxymethylphenyl)methanol;

[4-({[6-Ethyl-4'-(1-ethyl-1-hydroxypropyl)-2'-propylbiphenyl-3-yl]methylamino}methyl)-2-hydroxymethylphenyl]methanol;
[4-({Ethyl-[6-ethyl-4'-(1-ethyl-1-hydroxypropyl)-2'-propylbiphenyl-3-yl]amino}methyl)-2-hydroxymethylphenyl]methanol;
[4-({[6-Ethyl-4'-(1-ethyl-1-hydroxypropyl)-2'-propylbiphenyl-3-yl]propylamino}methyl)-2-hydroxymethylphenyl]methanol;
(4-{2-[6-Ethyl-2'-propyl-4'-(2,2,2-trifluoro-1-hydroxy-1-trifluoromethyl-ethyl)biphenyl-3-yl]ethyl}-2-hydroxymethylphenyl)methanol;
{4-[6-Ethyl-2'-propyl-4'-(2,2,2-trifluoro-1-hydroxy-1-trifluoromethyl-ethyl)biphenyl-3-yloxymethyl]-2-hydroxymethylphenyl}methanol;
{4-[6-Ethyl-2'-propyl-4'-(2,2,2-trifluoro-1-hydroxy-1-trifluoromethyl-ethyl)biphenyl-3-ylmethoxy]-2-hydroxymethylphenyl}methanol;
(4-{[6-Ethyl-2'-propyl-4'-(2,2,2-trifluoro-1-hydroxy-1-trifluoromethyl-ethyl)biphenyl-3-ylamino]methyl}-2-hydroxymethylphenyl)methanol;
[4-({[6-Ethyl-2'-propyl-4'-(2,2,2-trifluoro-1-hydroxy-1-trifluoromethyl-ethyl)biphenyl-3-yl]methylamino}methyl)-2-hydroxymethylphenyl]methanol;
[4-({N-Ethyl[6-ethyl-2'-propyl-4'-(2,2,2-trifluoro-1-hydroxy-1-trifluoromethyl-ethyl)biphenyl-3-yl]amino}methyl)-2-hydroxymethylphenyl]methanol;
[4-({[6-Ethyl-2'-propyl-4'-(2,2,2-trifluoro-1-hydroxy-1-trifluoromethyl-ethyl)biphenyl-3-yl]-N-propyl-amino}methyl)-2-hydroxymethylphenyl]methanol;
(4-{[4'-(1-Ethyl-1-hydroxypropyl)-6,2'-dimethylbiphenyl-3-ylamino]methyl}-2-hydroxymethylphenyl)methanol, and mixtures thereof.

4. A triaromatic vitamin D analogue having the structural formula (I) below:

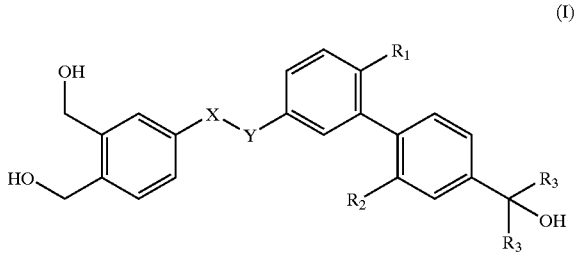

(I)

in which:
—X—Y represents the following structural bonds:
—CH$_2$—CH$_2$—
—CH$_2$—O—
—O—CH$_2$—
—CH$_2$—N(R$_4$)—
R$_4$ having the meanings given below,
—R$_1$ represents a methyl radical or an ethyl radical,
—R$_2$ represents an ethyl radical, a propyl radical or an isopropyl radical,
—R$_3$ represents an ethyl radical or a trifluoromethyl radical,
—R$_4$ represents a hydrogen atom, a methyl radical, an ethyl radical or a propyl radical, optical and geometrical isomers of the compounds of formula (I), and salts thereof wherein (i) —X—Y— represents —CH$_2$—CH$_2$—;
(ii) R$_1$ is an ethyl radical;
(iii) R$_2$ is a propyl radical; and
(iv) R$_3$ is an ethyl radical.

5. The vitamin D analogue as defined by claim 1, wherein formula (I):
(i) —X—Y— represents —CH$_2$—CH$_2$—;
(ii) R$_1$ is an ethyl radical;
(iii) R$_2$ is a propyl radical; or
(iv) R$_3$ is an ethyl radical.

6. A regime or regimen for treating:
1. dermatological disorders associated with a differentiation or proliferation disorder of keratinocytes or sebocytes;
2. keratinization disorders;
3. dermatological disorders associated with a keratinization disorder with an inflammatory and/or immunoallergic component;
4. inflammatory disorders not showing a keratinization disorder;
5. dermal or epidermal proliferations;
6. dermatological disorders such as bullous dermatoses and collagen diseases;
7. effects of aging of the skin, whether photo-induced or chronological aging, or for reducing actinic keratoses and pigmentations;
8. cicatrization disorders and stretch marks;
9. sebaceous function disorders; or
10. dermatological disorders with an immunological component, comprising administering to an individual subject in need of such treatment, for such period of time as required to elicit a desired therapeutic effect, a thus-effective amount of a vitamin D analogue as defined in claim 1.

7. The regime or regimen as defined by claim 6, comprising treating dermatological disorders associated with a differentiation or proliferation disorder of keratinocytes or sebocytes related to common acne, comedones, polymorphonuclear leukocytes, acne rosacea, nodulocystic acne, acne conglobata, senile acne, secondary acnes, solar acne, acne medicamentosa or occupational acne.

8. The regime or regimen as defined by claim 6, comprising treating keratinization disorders related to ichthyosis, ichthyosiform states, Darier's disease, palmoplantar keratoderma, leukoplakia conditions, leukoplakiform conditions, cutaneous lichen or mucous (buccal) lichen.

9. The regime or regimen as defined by claim 6, comprising treating dermatological disorders associated with a keratinization disorder with an inflammatory and/or immunoallergic concern, psoriasis, psoriatic rheumatism, cutaneous atopy, eczema, respiratory atopy or gingival hypertrophy.

10. The regime or regimen as defined by claim 6, wherein the dermal or epidermal proliferations are benign, malignant, of non-viral origin, of viral origin, common warts, flat wads, verruciform epidermodysplasia, oral papillomatoses, florid papillomatoses, proliferations induced by ultraviolet radiation, basocellular epithelioma, or spinocellular epithelioma.

11. A pharmaceutical composition comprising at least one vitamin D analogue as defined by claim 1, formulated into a therapeutically acceptable vehicle, diluent or carrier therefor.

12. The pharmaceutical composition according to claim 11, comprising from 0.001% to 5% by weight of said at least one vitamin D analogue.

13. A cosmetic composition comprising at least one vitamin D analogue as defined by claim 1, formulated into a cosmetically acceptable vehicle, diluent or carrier therefor.

14. The cosmetic composition according to claim 13, comprising from 0.001% to 3% by weight of said at least one vitamin D analogue.

15. A regime or regimen for preventing and/or treating photo-induced or chronological aging of the skin, comprising administering to an individual subject in need of such treatment, for such period of time as required to elicit a desired therapeutic effect, a thus-effective amount of the cosmetic composition as defined by claim 13.

16. The vitamin D analogue as defined by claim 2, wherein the mineral or organic acid is selected from the group consisting of hydrochloric acid, sulfuric acid, acetic acid, fumaric acid, hemisuccinic acid, maleic acid and mandelic acid.

17. The regime or regimen as defined by claim 6, wherein the sebaceous function disorders are selected from the group consisting of acneic hyperseborrhoea, simple seborrhoea and seborrhoeic eczema.

18. The regime or regimen as defined by claim 9, where the psoriasis is cutaneous psoriasis, mucous psoriasis or ungula psoriasis.

* * * * *